United States Patent [19]

Boyd et al.

[11] 4,075,492

[45] Feb. 21, 1978

[54] FAN BEAM X- OR γ-RAY 3-D TOMOGRAPHY

[75] Inventors: Douglas P. Boyd, Palo Alto, Calif.; Michael Goitein, Milton, Mass.

[73] Assignee: The Board of Trustees of Leland Stanford Junior University, Stanford, Calif.

[21] Appl. No.: 528,026

[22] Filed: Nov. 29, 1974

[51] Int. Cl.² .............................................. G01N 21/34
[52] U.S. Cl. .................................. 250/445 T; 250/385
[58] Field of Search ............................ 250/445 T, 385

[56] References Cited

U.S. PATENT DOCUMENTS

| | | | |
|---|---|---|---|
| 3,591,806 | 7/1971 | Brill et al. | 250/445 T |
| 3,654,469 | 4/1972 | Kantor | 250/385 |
| 3,684,886 | 8/1972 | Muehllegner | 250/445 T |
| 3,714,429 | 1/1973 | Mozley et al. | 250/445 T |
| 3,742,236 | 6/1973 | Richards | 250/445 T |

*Primary Examiner*—David C. Nelms

[57] ABSTRACT

A fan-shaped beam of penetrating radiation, such as X-ray or γ-ray radiation, is directed through a slice of the body to be analyzed to a position sensitive detector for deriving a shadowgraph of transmission or absorption of the penetrating radiation by the body. A number of shadowgraphs are obtained for different angles of rotation of the fan-shaped beam relative to the center of the slice being analyzed. The detected fan beam shadowgraph data is reordered into shadowgraph data corresponding to sets of parallel paths of radiation through the body. The reordered parallel path shadowgraph data is then convoluted in accordance with a 3-D reconstruction method by convolution in a computer to derive a 3-D reconstructed tomograph of the body under analysis. In a preferred embodiment, the position sensitive detector comprises a multiwire detector wherein the wires are arrayed parallel to the direction of the divergent penetrating rays to be detected. A focussed grid collimator is interposed between the body and the position sensitive detector for collimating the penetrating rays to be detected. The source of penetrating radiation is preferably a monochromatic source.

21 Claims, 22 Drawing Figures

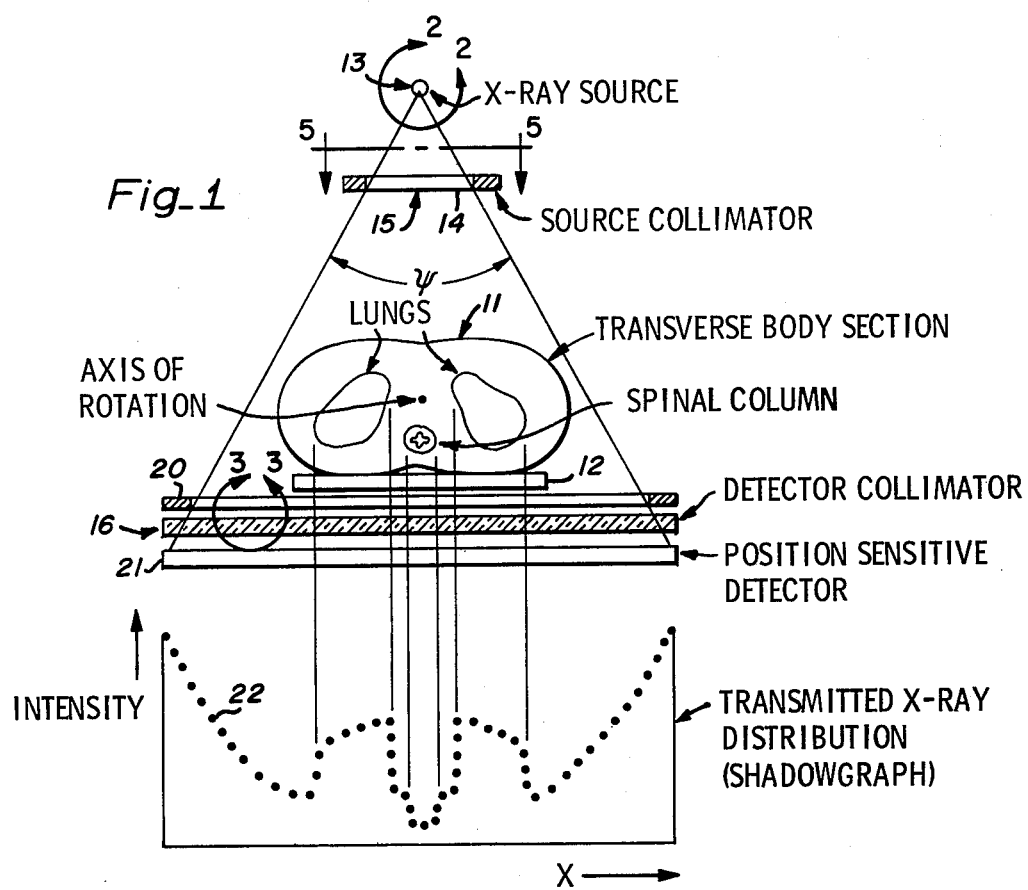
Fig_1
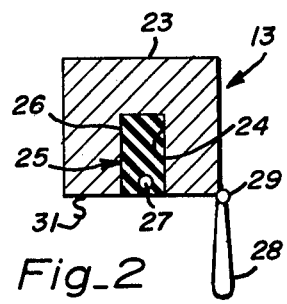
Fig_2
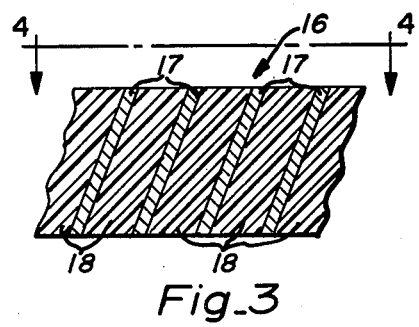
Fig_3
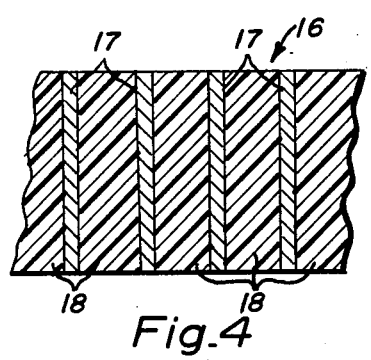
Fig_4
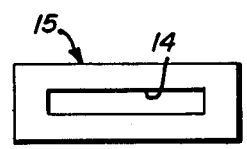
Fig_5

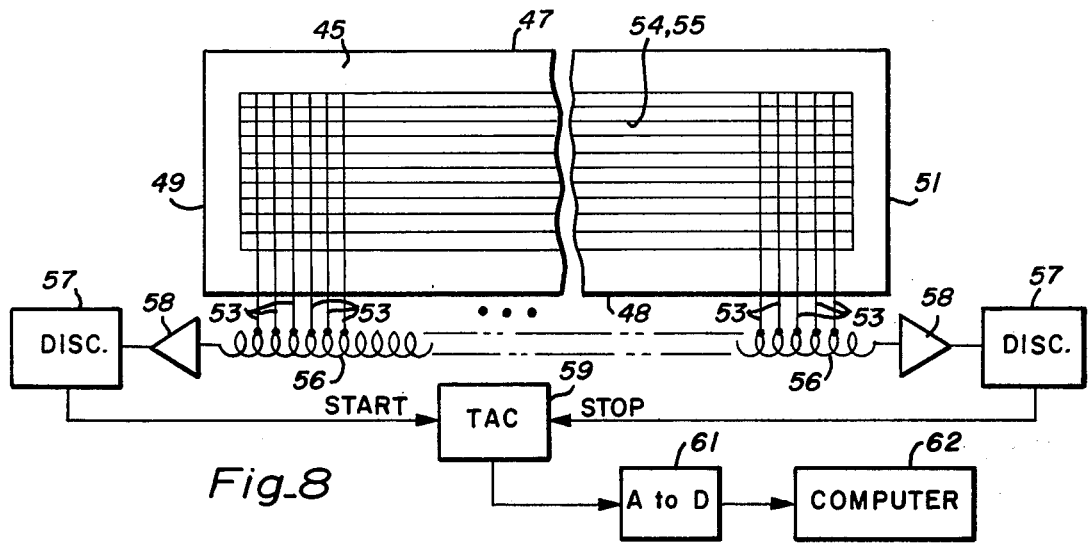
Fig_8
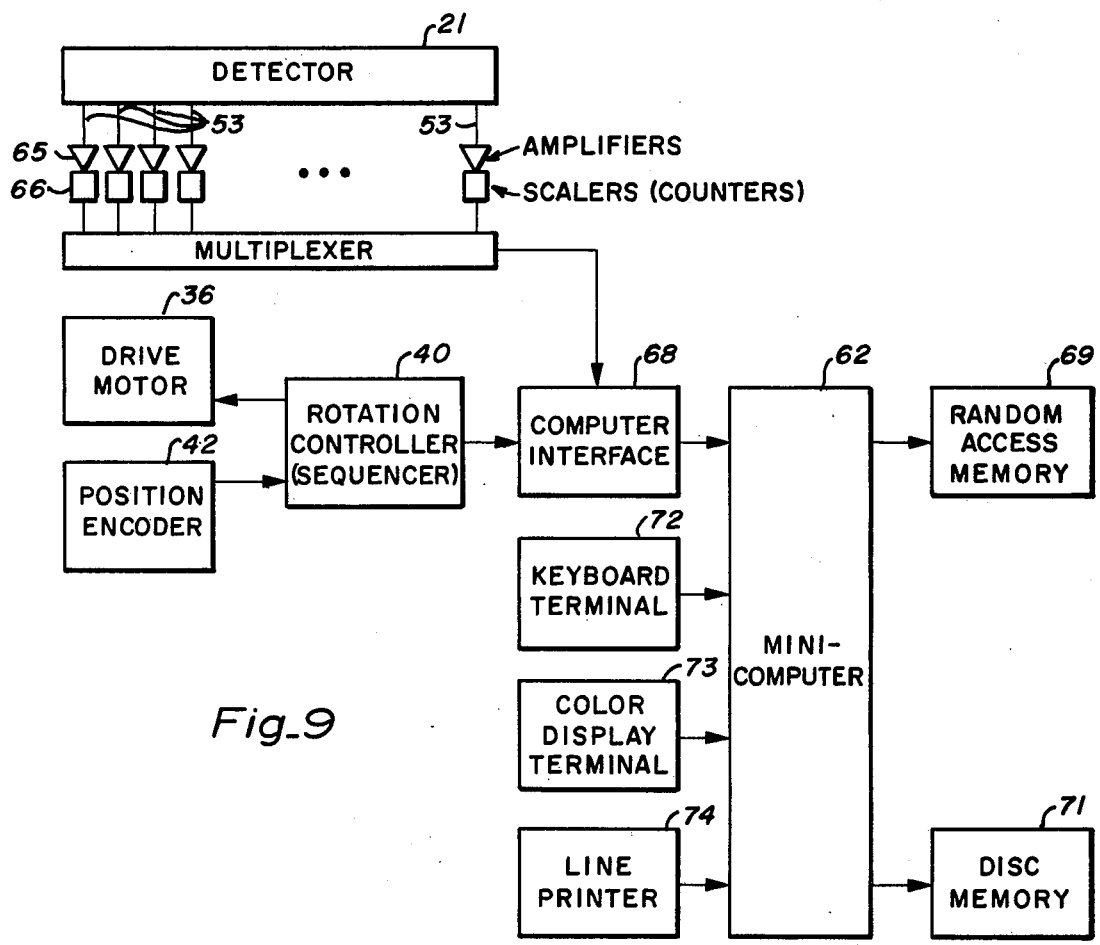
Fig_9

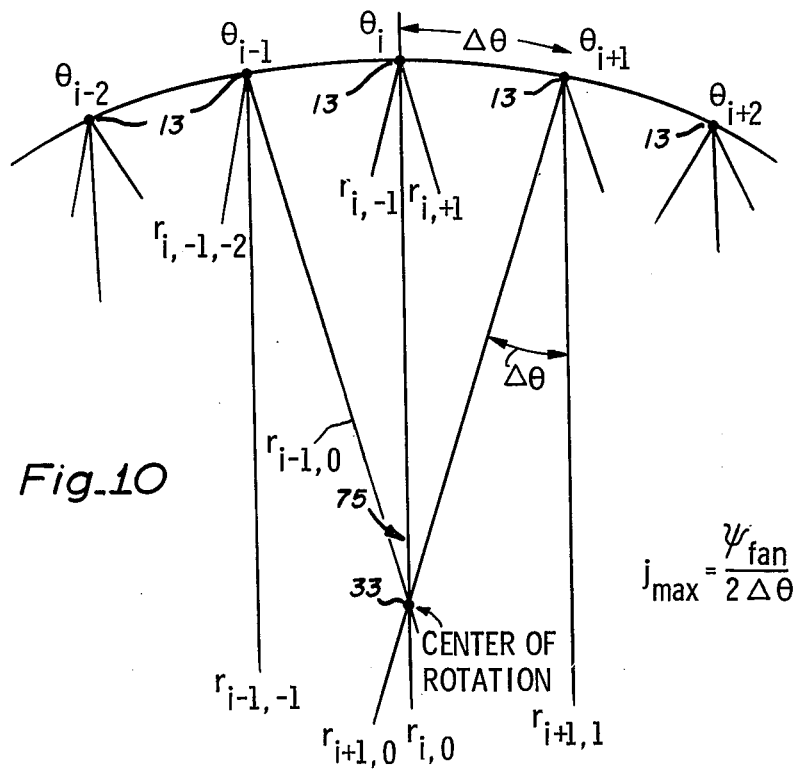
*Fig. 10*
$$j_{max} = \frac{\psi_{fan}}{2\Delta\theta}$$
$\theta_i$ SERIES:
$$r_{i-j_{max},-j_{max}} \cdots r_{i-1,-1}; r_{i,0}; r_{i+1,1} \cdots r_{i+j_{max},j_{max}} \rightarrow \theta_i$$
$\theta_{i+1}$ SERIES:
$$r_{i+j_{max}+1,-j_{max}} \cdots r_{i-1,-1}; r_{i-1}; r_{i+1,0}; r_{i+2,1} \cdots r_{i+j_{max}+1,j_{max}} \rightarrow \theta_{i+1}$$
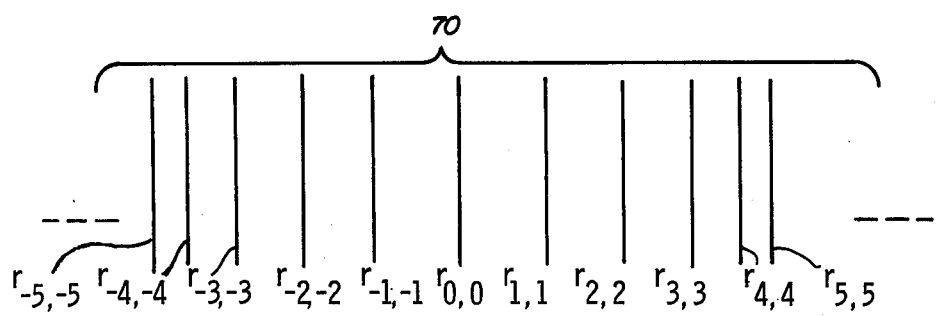
*Fig. 12*
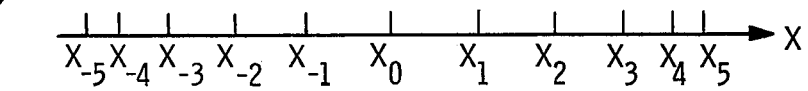
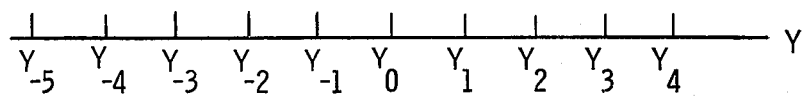

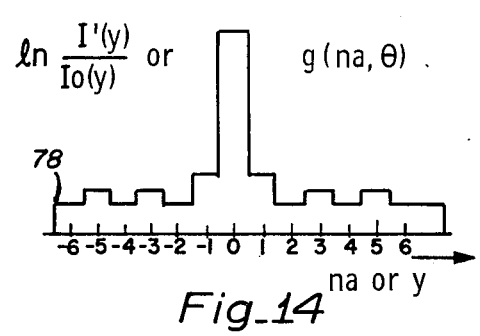
Fig_14
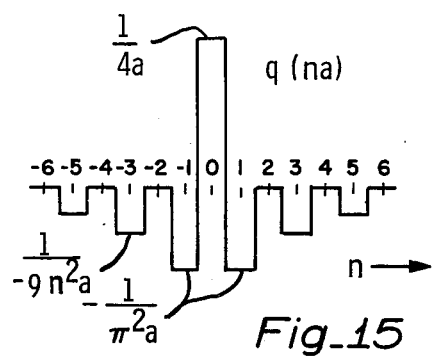
Fig_15
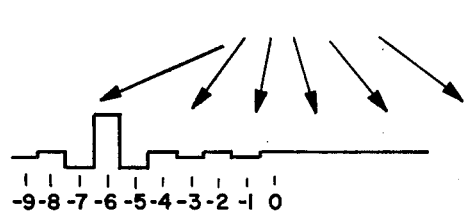
Fig_16
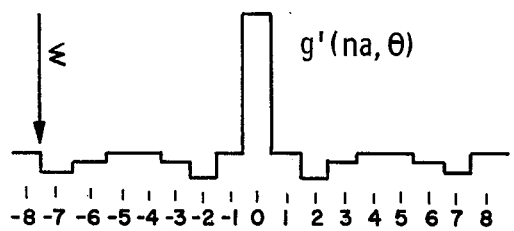
Fig_17
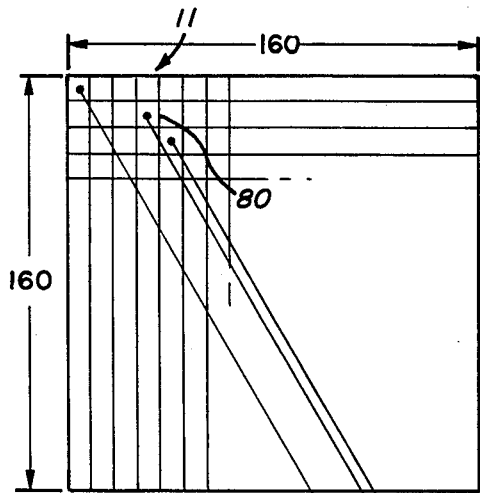
Fig_18
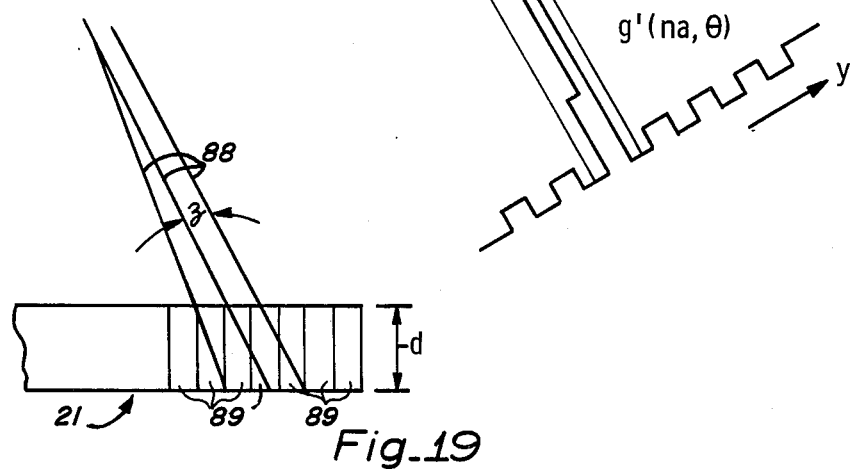
Fig_19

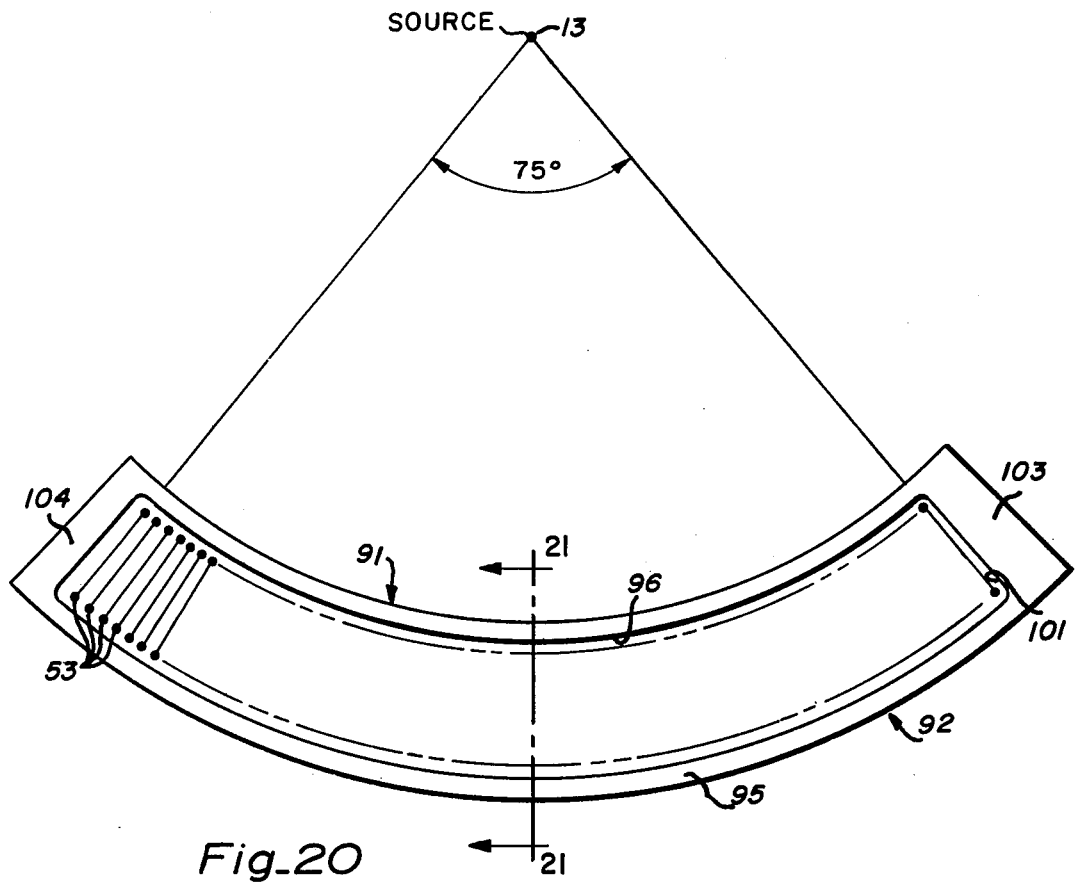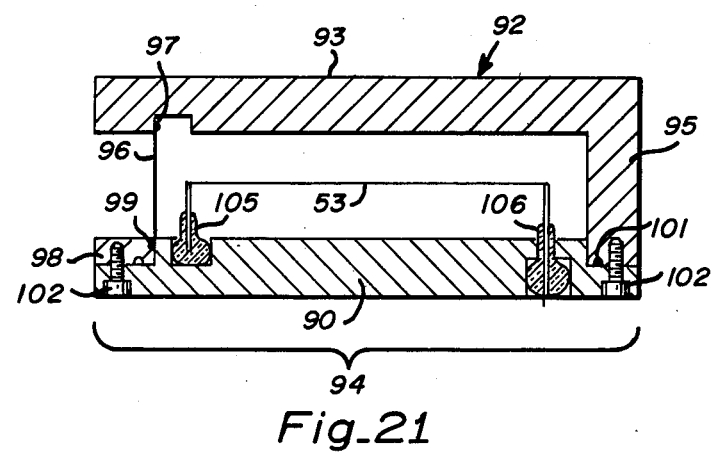

FAN BEAM X- OR γ-RAY 3-D TOMOGRAPHY

GOVERNMENT CONTRACT

The Government has rights in this invention pursuant to grant number GI-35007 awarded by the National Science Foundation.

RELATED CASES

A multiwire radiation detector, of the type wherein the wires of the detector are parallel to the divergent rays of penetrating radiation, forms the subject matter of and is claimed in copending U.S. application Ser. No. 528,025 filed Nov. 29, 1975 and assigned to the same assignee as the present invention. The method and apparatus for reconstructing a 3-D tomograph from divergent path fan beam data reordered to parallel ray data, and including the method of 3-D reconstruction by convolution, forms the subject matter of and is claimed in copending U.S. patent application Ser. No. 528,024 filed Nov. 29, 1975 and assigned to the same assignee as the present invention.

BACKGROUND OF THE INVENTION

The present invention relates in general to fan beam X- or γ-ray 3-D tomography and more particularly to such tomography utilizing a position sensitive detector.

DESCRIPTION OF THE PRIOR ART

Heretofore, it has been proposed to employ collimated beams of penetrating radiation to derive a set of angularly displaced shadowgraph data from which to reconstruct a 3-D tomograph of a slice of the body. The 3-D tomograph was reconstructed by a method of computing the absorption or transmission coefficients for a matrix of elements of cross sectional area intersected by the angularly displaced sets of parallel rays. The coefficients were refined by a process of successive approximations to derive the final 3-D tomograph. Such a method is proposed in U.S. Pat. No. 3,778,614 issued Dec. 11, 1973.

In this prior patent, the shadowgraph data is derived by either of two methods. In a first method, a collimated source of penetrating radiation passes through the body to a detector in alignment with the beam path. The detector and source are then rectilinearly translated laterally relative to the body to derive a given set of shadowgraph data. The source and detector are then angularly rotated to a second position and again laterally translated relative to the body to obtain a second set of shadowgraph data, and so forth.

In the second method, a fan-shaped array of collimated beams of penetrating radiation, each beam having a detector in alignment therewith, is caused to be laterally rectilinearly translated relative to the body and then rotated to a second position with lateral translation at the second position, and so forth and so on, to derive angularly displaced sets of shadowgraph data.

The advantage of the second scheme relative to the first scheme, is that the lateral translation can be cut by a factor of 1/N where N is the number of detectors, such as 5 or 7. However, this prior art patent discloses that the paths of penetrating radiation through the body should all have a constant width and that this is an essential requirement for accurate computer calculations which are to follow for reconstruction of the 3-D tomograph. Also, the algorithms presented therein for reconstruction of the 3-D tomograph are based upon sets of parallel rays. However, in the case of the collimated divergent beams, there is no disclosure of how one obtains shadowgraph data based upon sets of parallel rays. Furthermore, there is no teaching nor suggestion of how the divergent rays passing through the body could be made to transverse paths of constant width. Thus, there is no teaching in the subject patent of a method for reconstruction of 3-D tomographs from sets of divergent rays of penetration as would be obtained from a divergent fan beam.

SUMMARY OF THE PRESENT INVENTION

The principal object of the present invention is the provision of method and apparatus for reconstructing 3-D tomographs employing a divergent fan beam of penetrating radiation.

In one feature of the present invention, a method and apparatus for penetrating ray 3-D tomography is provided which employs a fan-shaped beam of divergent penetrating radiation, whereby the time required to expose a body to penetrating radiation to derive the data for reconstructing a 3-D tomograph is substantially reduced, such as to a breath-holding period, thereby permitting 3-D tomographs to be reconstructed of a patient's midsection.

In another feature of the present invention, a position sensitive detector for detecting the fan-shaped beam of divergent rays of penetrating radiation comprises an envelope containing an ionizable gaseous atmosphere and an array of spaced anode and cathode electrodes for generating an electrical output signal in response to an ionizing event occasioned by absorption of a quantum of penetrating radiation by the ionizable gas.

In another feature of the present invention, a penetrating ray collimator is interposed between the body under examination and the position sensitive detector for collimating the rays of penetrating radiation emerging from the body under examination.

Other features and advantages of the present invention will become apparent upon a perusal of the following specification taken in connection with the accompanying drawings wherein:

BRIEF DESCRIPTION OF THE DRAWINGS

FIG. 1 is a schematic transverse sectional diagram of a penetrating ray 3-D tomography apparatus of the present invention and including a shadowgraph produced by the apparatus, FIG. 2 is an enlarged sectional view of a portion of the structure of FIG. 1 delineated by line 2—2.

FIG. 3 is an enlarged detail view of a portion of the structure of FIG. 1 delineated by line 3—3.

FIG. 4 is a view of the structure of FIG. 3 taken along line 4—4 in the direction of the arrows, FIG. 5 is an enlarged detailed view of a portion of the structure of FIG. 1 taken along line 5—5 in the direction of the arrows FIG. 8 is a view of the structure of FIG. 7 taken along line 8—8 in the direction of the arrow and including associated circuitry in block diagram form, FIG. 9 is a schematic line diagram, partly in block diagram form, or a data processing portion of the apparatus of the present invention, FIG. 10 is a schematic line diagram depicting how a rotating fan beam produces sets of parallel rays, FIG. 12 is a schematic diagram depicting the process for correction of the set of detected parallel rays to sets of parallel ray data of equal lateral spacing, FIG. 14 is a shadowgraph converted to 1n of the ratio of detected intensity as a function of lateral position I' (y) divided by the beam intensity Io measured without absorption, FIG. 15 is a plot of function utilized in the 3-D reconstruction method, FIG. 16 is a plot for the convolution of the function of FIG. 15 with a single point on the function of FIG. 14, FIG. 17 is a plot of the convolution of the function of FIG. 15 with the shadowgraph function of FIG. 14, FIG. 18 is a schematic line diagram depicting the process for back projecting and adding the contributions of the convoluted spectrographic data, FIG. 19 is a schematic line diagram representing the positional uncertainty when a fan beam is detected by a rectilinear detecting array, FIG. 20 is a longitudinal sectional view of a preferred multiwire radiation detector, FIG. 21 is an enlarged sectional view of the structure of FIG. 20 taken along line 21—21 in the direction of the arrows.

DESCRIPTION OF THE PREFERRED EMBODIMENTS

Figure 6:
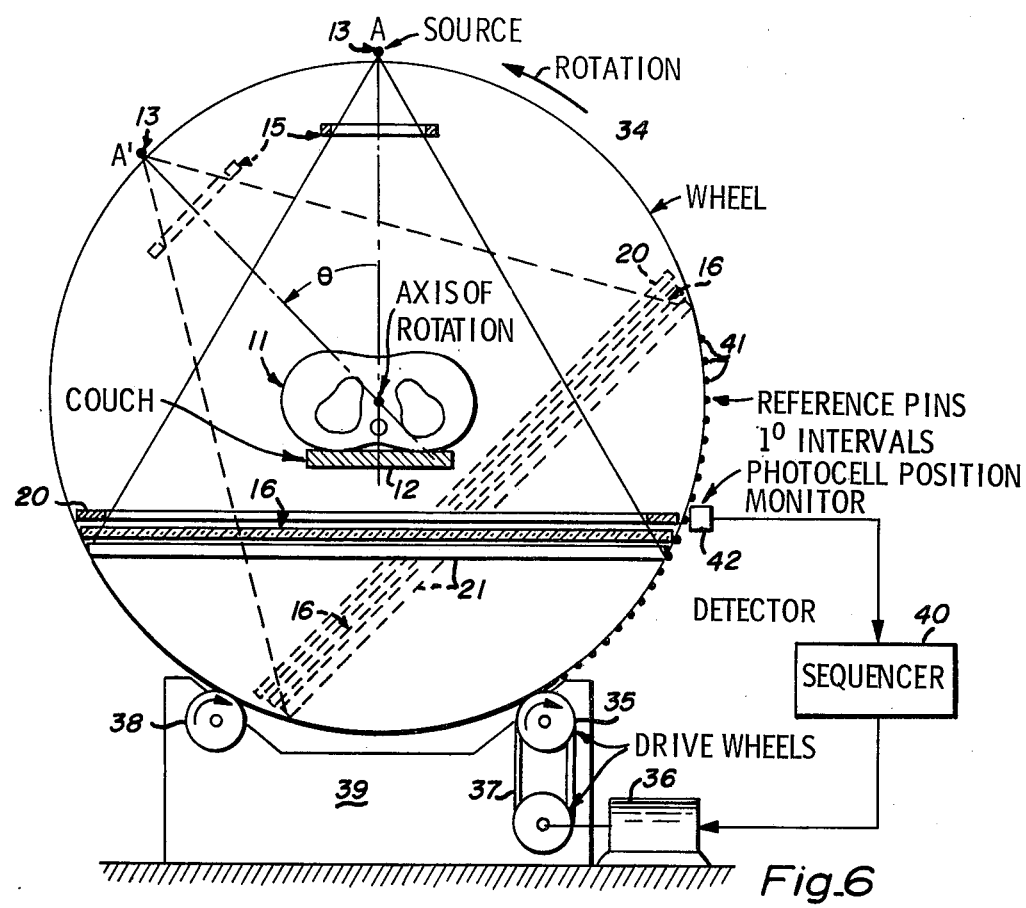
FIG. 6 is a schematic diagram of a fan beam X-ray 3-D tomographic apparatus incorporating features of the present invention.

Referring now to FIG. 1, there is shown an apparatus for deriving penetrating radiation shadowgraphs of a body to be examined. More particularly, the patient 11 to be examined is supported on a couch 12, as of a suitable plastic material. A suitable point source of penetrating radiation 13, such as X-rays or γ-rays is disposed above the body for projecting a fan-shaped beam of divergent penetrating radiation through a narrow elongated slot 14 in a collimator 15, as of lead. The fan-shaped beam is relatively thin and comprises divergent rays of penetrating radiation which are directed onto the body 11 to be examined.

The penetrating radiation is partially absorbed in the body 11 in accordance with the density of the various portions of the body penetrated by the radiation. In a typical example of a torso tomograph, the lungs would have relatively low density, whereas the spinal column would have relatively high density. The penetrating radiation emerging from the body is passed through a second fan beam collimator 20 and thence through a focussed grid collimator 16 which is shown in greater detail in FIGS. 3 and 4. The second collimator 20 is similar to the fan souce collimator 15 and the focussed grid collimator 16 comprises an array of lead vanes 17 embedded in a plastic filllter material 18, as of polyethylene. The vanes 17 have a thickness of, for example, 0.5 millimeters and the plane of the vanes is directed parallel to the divergent rays emanating from the source 13. In a typical example, the collimating vanes 17 are spaced apart by approximately 5.0 millimeters for blocking scattered radiation emerging from the body 11 from passing into a position sensitive radiation detector 21. Less than 1% of the scattered radiation reaches the detector 21.

In a preferred embodiment, the position sensitive detector 21 includes an array of closely spaced detecting wires as more fully disclosed below with regard to FIGS. 7, 8, 9, and 20 and 21. Generally, there is one detecting element of the array in alignment with the center of each of the bins of collimated divergent rays passing through the collimator 16. In a typical example, the position sensitive detector 21 would have a length of approximately 50 centimeters and would include 150 individual detecting elements at $\frac{1}{2}$° intervals. The fan beam typically subtends an arc $\psi$ of 75°.

The penetrating radiation such as X-rays or γ-rays, in passing through the body 11, are variously attenuated or absorbed by the different portions within the body such as the lungs, spinal column, etc. to produce a shadowgraph of detected intensity versus distance as shown in FIG. 1 by curve 22.

In a typical example, the X-ray or γ-ray source 13, which is shown in greater detail in FIG. 2 comprises a cylindrical body 23 of high atomic number Z material, such as lead or tantalum, and includes a central reentrant bore 24 containing a cylindrical insert 25. The insert typically comprises a plastic body 26 having a pellet 27 of radioactive material embedded in the outer end thereof. A shutter 28 of high Z material is pivotably mounted to the body 23 at 29 and is pivoted for closing off the source of radiation and held in the closed position via a spring clasp 31. Typical source materials for the pellet 27 include materials that will provide X-ray or γ-ray radiation having intensities falling within the range of 50-100 keV. The source radiation is preferably monochromatic. Materials of this type include Gadolinium$^{153}$ having a half life of approximately 242 days and having a very stable predictable decay rate. However, other types of sources 13 could be employed such as an X-ray tube utilizing various different types of secondary γ- or X-ray emitting materials.

Referring now to FIG. 6 there is shown the apparatus of FIG. 1 mounted for rotation about an axis of rotation 33 disposed centrally of the body 11. The source 13, detector 21, and collimator 16 are mounted to a ring 34 for rotation about the axis of rotation 33. The ring 34 is driven from a friction drive wheel 35 which is connected to a drive motor 36 via a suitable drive means, such as a drive belt 37. The ring 34 is supported via the drive wheel and an idler wheel 38 rotationally mounted to a base support structure 39. The ring 34 includes an array of axially directed pins 41 disposed at 1° intervals around the periphery of the ring 34. A photocell detector 42 is mounted in fixed relation relative to the ring 34 and pins 41 so that as the ring 34 is rotated successive pins 41 come into registration with the optical path of reflected light from the respective pin 42 to the photocell 42 for giving an output signal indicative of the angular position of the ring 34 and, thus, the source and detector relative to the body 11.

This electrical signal, representative of the position of the ring 34, is fed to one input of a sequencer 40. The output of the sequencer 40 is fed to the motor 36 for driving the ring 34 around the body 11. For each one degree of angular position θ, a 151 point shadowgraph is derived so that a set of shadowgraphs is obtained there being one shadowgraph for each degree of rotation of the source around the patient. In a typical example employing a 75° fan beam of radiation, the sequencer 40 is set to rotate the source continuously around the patient for a total of 225° to obtain 255 sets of shadowgraph data. The reason for 255 sets of data is explained below.

Figure 7:
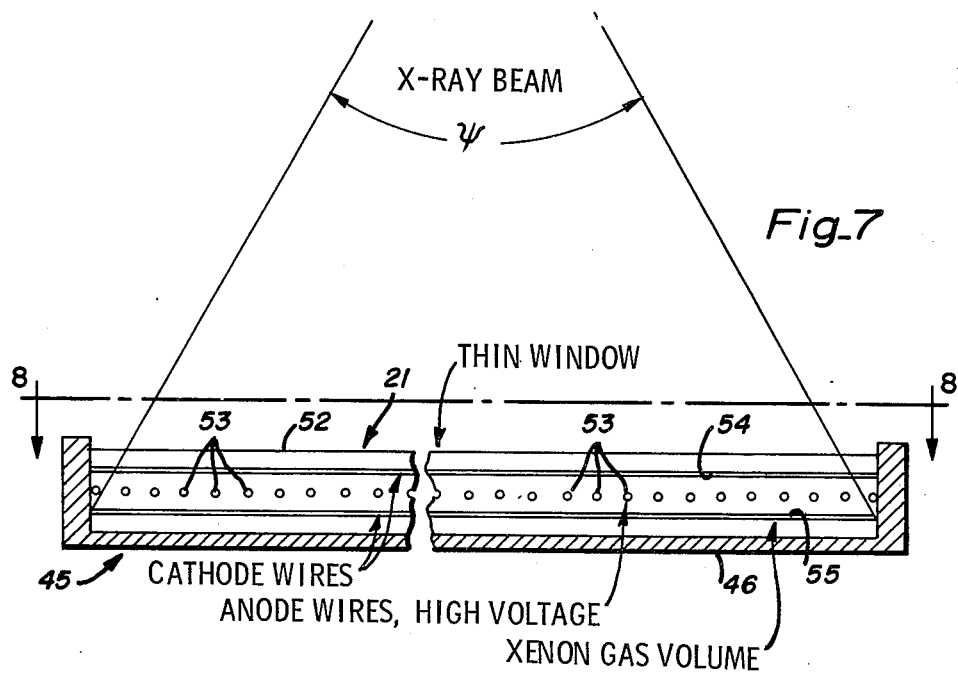
FIG. 7 is a longitudinal sectional view of a position sensitive X-ray detector employed in the apparatus of the present invention.

Referring now to FIGS. 7 and 8 there is shown a position sensitive detector 21. The detector includes an elongated channel member 45, as of G-10 fiberglass, having a base portion 46 and two upstanding side wall portions 47 and 48. The channel 45 is closed at its ends via transverse walls 49 and 51. In a typical example, the detector 21 has a length of 50 centimeters. A penetrating ray transparent gas-tight window 52, as of Mylar, is sealed across the open side of the channel 45. An array of transversely directed anode wires 53 extend for the length of the detector 21. Two arrays of longitudinally directed cathode wires 54 and 55 are disposed on opposite sides of the anode array 53.

In a typical example, the anode wires 53 are spaced apart by 2.5 millimeters and the wires have a diameter of 0.025 millimeters (25 microns). The cathode wires 54 and 55 are of tungsten having a diameter of 0.1 millimeters and are spaced apart by approximately 2.5 millimeters. The cathode wires are operated at ground potential, whereas the anode wires 53 are operated at +3kV. The chamber defined by the interior of the closed channel 45 is filled with an ionizable gaseous medium such as Xenon at atmospheric pressure. The cathode wires are spaced above and below the anode wires by approximately 3 millimeters.

The anode wires 53 pass through the side wall 48 of the channel 45 in gas tight sealed relation therewith and are affixed at equally spaced intervals to and along a helical delay line 56 operating at anode potential. Opposite ends of the delay line 56 are connected to respective pulse discriminators 57 via the intermediary of pulse amplifiers 58. The outputs of the discriminators 57 are fed to a time-to-amplitude converter 59 which coverts the timing between successive pulses, as derived from the discriminators 57, to a potential proportional to the timing between such pulses. The potential output of the time-to-amplitude converter 59 is fed to one input of an A-to-D converter 61 for converting the amplitude information to a digital output which is thence fed to a computer 62 which will be more fully described below.

In operation, a quantum ionizing radiation passing through the body 11 passes through the window 52 and into the ionizable gas filled chamber 45. Due to the high electrical field region surrounding the individual anode wires 53, when a quantum of ionizing radiation is absorbed in the ionizable gas, ionization occurs which triggers an avalanche of current flow between the anode and cathode resulting in a current pulse on the respective anode wire 53 which is closest to the ionizing event. That pulse of avalanche current is fed onto the delay line at the corresponding connection of that anode wire with the delay line 56. The pulse of current travels in opposite directions along the delay line 56 to the ends thereof and thence via the amplifiers 58 into the discriminators 57.

The discriminators 57 produce corresponding output pulses corresponding to the leading edge of the respective current pulses. The time difference between successive pulses is proportional to or otherwise representative of the position of the ionizing event as detected by the closest anode wire 53. The pulses are thence fed into the time-to-amplitude converter 59 for producing an output potential corresponding to the position of the ionizing event. This potential is thence converted to digital data in the analog-to-digital converter 61 and fed to the computer 62. The computer stores the ionizng event in a respective channel corresponding to the position of the ionizing event. Subsequent ionizing events detected during the measurement of one shadowgraph for each angle of θ are stored in their respective channels. Thus, the computer has stored in its memory, after one rotation of the source through 255°, 255 sets of shadowgraph data. The computer will then utilize these sets of shadowgraph data for reconstructing a 3-D tomograph of the section of the body 11 under examination, as more fully described below.

One of the problems with the delay line type of position sensitive detector 21, as shown in FIGS. 7 and 8, is that it is limited to a counting rate of approximately $10^5$ counts of ionization events per second. It is desired to employ a detector which is capable of counting at a rate of $10^8$ events per second or higher. For example, in order to obtain a 3-D tomograph having a one-half percent precision in the density, approximately $10^9$ counts per second are required. It is desirable that the 3-D tomograph data be acquired during one breath-holding period, i.e., a time of approximately 15 seconds or less. This then leads to a desired counting rate of at least $10^8$ per second.

The counting rate can be increased to at least $10^8$ per second by deleting the delay line 56 and connecting each of the individual anode wires 53 to a respective amplifier 65 and counter 66, as shown in FIG. 9. The outputs of the counters 66 are fed to an input of a multiplexer 67 such that upon the completion a shadowgraph for each angular position of θ, the data in the counters 66 is read out via the multiplexer 67 into the computer 62 via a computer interface 68. The computer 62 may comprise, for example, a PDP 11/45 minicomputer provided with a random access memory 69 and a disc memory 71. In addition, the minicomputer 62 provides a keyboard terminal 72, and a color display terminal 73, wherein contours of a given density in the 3-D tomograph are displayed with different given colors, such that density differentiation is enhanced to the human eye. In addition, the minicomputer includes a line printer 74 for printing out a 3-D density tomograph in terms of numbers corresponding directly to density.

Referring now to FIGS. 10–19 and to the flow charts of FIG. 22 the computer method for reconstructing the 3-D tomographs from the sets of angularly displaced shadowgraph data will be explained in greater detail. The sets of shadowgraph data, as detected by the position sensitive detector 21, are generated by absorption of penetrating radiation by the body under analysis as taken along an array of divergent paths or rays. The preferred 3-D tomograph reconstruction method requires that the shadowgraph data correspond to absorption of penetrating radiation along an array of parallel paths or rays.

It has been found that the detected divergent path shadowgraph data can be reordered into sets of shadowgraph data representative of that obtained by arrays of parallel rays. This reordering process for reordering the divergent ray shadowgraph data into parallel ray shadowgraph data is illustrated in FIG. 10. In position of the source 13 projects a fan-shaped beam over a continuous distribution of divergent paths contained within the angle $\psi$ subtended by the fan-shaped beam. If we consider the central path or ray 75 which is identified $r_{i,0}$ it is seen that this ray passes through the axis of revolution 33 to the detector. Other rays denoted by $r_{i,-37}, r_{i,-36}, \ldots r_{i,+37}$ are spaced at 1° intervals within the fan. When the source 13 of the fan-shaped beam is rotated in the positive $\theta$ direction by one degree about the axis of rotation 33 and from the initial position of $\theta i$ to $\theta i + 1$, it will be seen that there is a new central ray identified as $r_{i+1,0}$ which is displaced from $r_{i,0}$ by 1° and which passes through the axis of rotation 33. In addition, there is a ray $r_{1,1}$ which is parallel to $r_{i,0}$. Likewise, when the source 13 is rotated 2° to $\theta i + 2$ there is a ray $r_{i+2,2}$ parallel to both $r_{i,0}$ and $r_{i+1,1}$. Following this rationale it will be seen that there are sets of parallel rays according to the series indicated in FIG. 10 where $r$ is a ray or path and has subscripts $\theta$ and $\psi$ where $\theta$ is the angular position of the source 13 and $\psi$ is the angular displacement of the ray from the center ray of the fan-shaped beam.

Rays may be labelled as $r_{i,j}$ where $i$ is an index defining the position of the source ($\theta_i = i\Delta\theta$) and $j$ is an integer denoting the position of each ray within a particular fan. The central ray of the fan passes through the center of rotation and is denoted by $j=0$. Adjacent rays are numbered consecutively. Referring to FIG. 10 it can be seen that it is possible to obtain at least two arrays of parallel rays as shown. If we denote a series of parallel rays inclined at $\theta_i$, $i = 0 \ldots 180/\Delta\theta$, by $r'_{ij}$ then the reordering process can be generalized by the following transformation where $\psi$ fan is and odd multiple of $\Delta\theta$:

$$r'_{ij} = r_{i+j,j} \quad j = -j_{max} \ldots +j_{max}$$

where $j_{max} = (\psi \text{ fan} - 1)/2\Delta\theta$. For the particular case $\Delta\theta = 1°$ and $\psi$fan$=75°$, then 180 sets of parallel rays are formed with $i = 0, \ldots, 179$.

Although in the above discussion for convenience the position of the source 13 was depicted as located at particular points, and the rays represented by lines, it should be understood that the source 13 and detectors 21, etc., rotate at constant angular velocity and data is accumulated during intervals during which the source moves continuously from one position to the next, so that $\theta$ represents a mean source position during a particular interval in time. Likewise, the detector 21 is sensitive to the continuous distribution of transmitted radiation so that rays really represent the average transmission in a region of narrow width bounded by neighboring rays.

For relatively high resolution it is desired to obtain 180 sets of parallel rays at one degree $\theta$ intervals. It can be shown that if 180 sets of such parallel rays are to be obtained the source 13 must be rotated through a total angle $\theta$ of 180° plus the fan angle $\psi$fan. In the case of a fan angle $\psi$fan of 75°, the total angular displacement $\theta$ is 255°. Thus, the 255 sets of divergent path or ray shadowgraph data are reordered by the computer 62 into 180 sets of parallel ray shadowgraph data. The reordering may be accomplished by the computer 62 after the divergent ray shadowgraphic data is stored in the respective channels of the memory or the data, as it is obtained at the detector 21 and multiplexed into the memory of the computer 62, is addressed in accordance with the desired reordering address method so that the data, as initially stored, is stored in sets of parallel shadowgraphic data.

Figure 11:
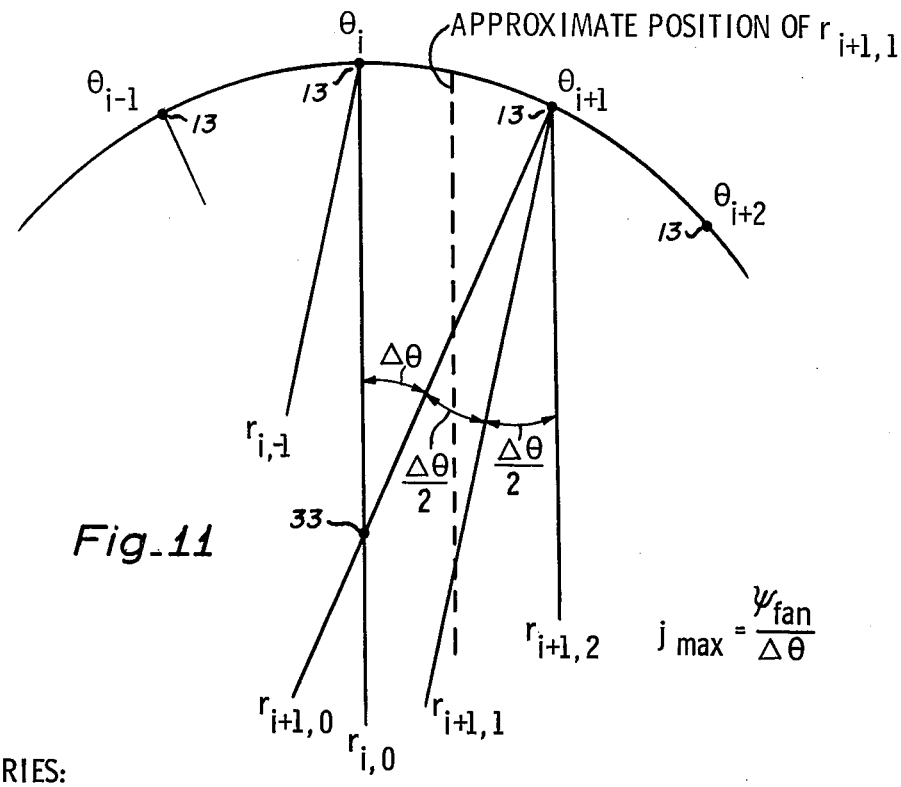
FIG. 11 is a view similar to that of FIG. 10 depicting extrapolation of the arrangement of FIG. 10 to twice as many detectors and to approximations of parallelism for the added intermediate rays.

In order to optimize the spatial resolution that can be achieved with a given finite number of measurements it is found that the fan rays must be more closely spaced than the rotation step angle $\Delta\theta$. If this spacing is chosen to be a fractional value of $\Delta\theta$, say $\Delta\theta/n$ where $n = 2, 3, 4$ then the above reordering process can still be used providing a slant approximation is introduced. A preferred value of $n$ is 2 yielding $\Delta\psi = \frac{1}{2}°$ if $\Delta\theta = 1°$. FIG. 11 illustrates how sets of parallel rays are obtained from fan rays in this case. The slant approximation is introduced as follows. Ray $r_{i+1,1}$ is selected to be a member of the series of rays parallel to $r_{i,0}$ with spacing midway between $r_{i,0}$ and $r_{i+1,2}$. It has been found that this approximation introduces a negligible loss of spatial resolution in the reconstruction. Two sets of parallel rays are indicated in FIG. 11 at $\theta_i$ and $\theta_{i+1}$. Thus for $n=2$ and using the slant approximations the reordering transformation becomes:

$$r'_{ij} = r_{i+*/2, j} \quad j = j_{max}, \ldots j_{max}^{-1},$$

and $j_{max} = \psi$fan$/\Delta\theta$. Here $j^*$ refers to an even integer which may be either $j$ or $j+1$.

Also it can be shown that the sets of reordered parallel paths or rays are not of equal lateral spacing. The spacing decreases with distance away from the central ray. This is depicted in FIG. 12, where the $x$ abscissa scale represents the spacings of the reordered sets of parallel rays. The preferred 3-D method of reconstruction employs data based upon uniform lateral spacing between parallel rays of the set. Therefore, it is desired to modify the sets of reordered parallel ray shadowgraphic data into such data having equal lateral spacing between all parallel rays of the set.

Figure 13:
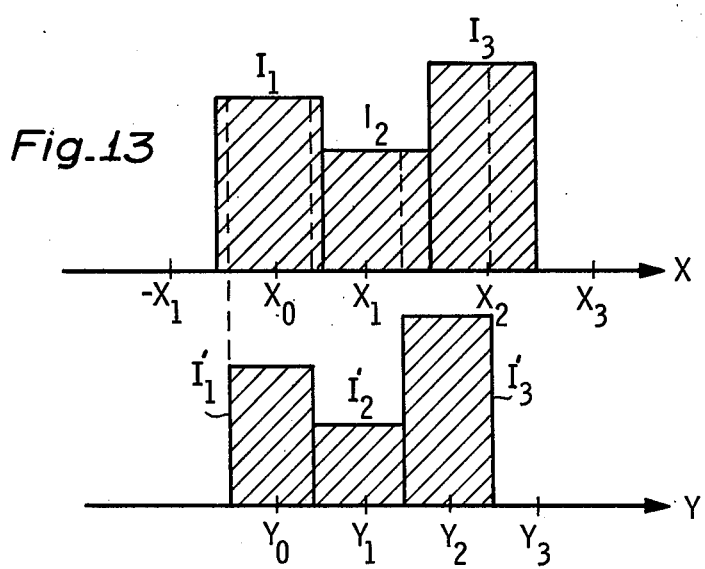
FIG. 13 is a schematic diagram depicting the process for compensating for non-equal spacing between the detected parallel rays.

Referring now to FIGS. 12 and 13 there is shown the method for transforming the parallel ray shadowgraphic data into such data having equal lateral spacing. A set of parallel rays of unequal spacing is shown at 70 in FIG. 12. In this example $n=1$, i.e., the slant approximation is not used, and $\Delta\theta = 1°$. The $x$ designated abscicca scale shows the unequal lateral spacing where $x_0 = 0$, $x_1 = R\sin 1°$, $x_2 = R\sin 2° \ldots x_j = R\sin j\Delta\theta$ where $R$ is the radius of the circle of revolution of the source 13 relative to the body 11 and $j$ is the number of the ray from the centray ray. The abscissa scale for equal lateral spacing of the rays 70 is that indicated by $y$, where $y_1 = a$, $y_2 = 2a$, $y_3 = 3a \ldots y_n = na$ where $a = X_{max}/n$. In the case of $\psi = 75°$ then $a = [R\sin 37/37] = [R\sin (j_{max} \Delta\theta/j_{max} \Delta\theta]$.

The detected radiation intensity $I_1, I_2, \ldots I_n$ is based upon parallel rays of unequal lateral spacing, i.e., they have the $x$ abscissa scale as shown in FIG. 13. Here the radiation intensity is assumed to be uniform within bins bounded by the midpoints between rays as shown, and the area of bins represent the measured radiation intensities $I_i$. The $x$ scale intensities $I_1, I_2, I_3 \ldots I_n$ may be transformed by a rebinning process to derive parallel ray shadowgraphic intensities $I'_1, I'_2 \ldots I'_n$ of equal lateral spacing, as follows.

The new intensities are determined by the amount of area in old bins overlapped by new bins. For example, $$\Gamma_1 = \frac{a}{x_1} I_1 \qquad \text{(Eq. 1)}$$

and, $$\Gamma_2 = \left(\frac{x_1 - a}{2x_1}\right) I_1 + \left(\frac{3_a - x_1}{x_2}\right) I_2 \qquad \text{(Eq. 2)}$$

$$\Gamma_3 = \left(\frac{x_1 + x_2 - 3a}{x_2}\right) I_2 + \left(\frac{5a - x_1 - x_2}{x_3 - x_1}\right) I_3 \qquad \text{(Eq. 3)}$$

This process may be generalized by the equation:

$$\Gamma_i(y) = \sum_j f_{ij} I_j(x) \qquad \text{(Eq. 4)}$$

where $f_{ij}$ are the coefficients in the above equations (Eq. 1-3) and represent the fractional overlap of new bins with old bins as determined by simple geometry as illustrated above. For speed and convenience these may be calculated in advance and stored in a disk file which may be used by the reconstruction program. Although usually the above series of equations contain only two terms, occasionally three terms will be present corresponding to the case in which a new bin as illustrated in FIG. 13 ($y$ axis) is overlapped by three old bins. In the case of use of a slant approximation with $n = 2,3,4$ rebinning may proceed as above except that the values of the coordinates are given by $x_j = R\sin j\Delta\theta/n$ and $$a = \frac{2R}{n\psi_{fan}} \sin(\psi_{fan}/2).$$

Figure 22:
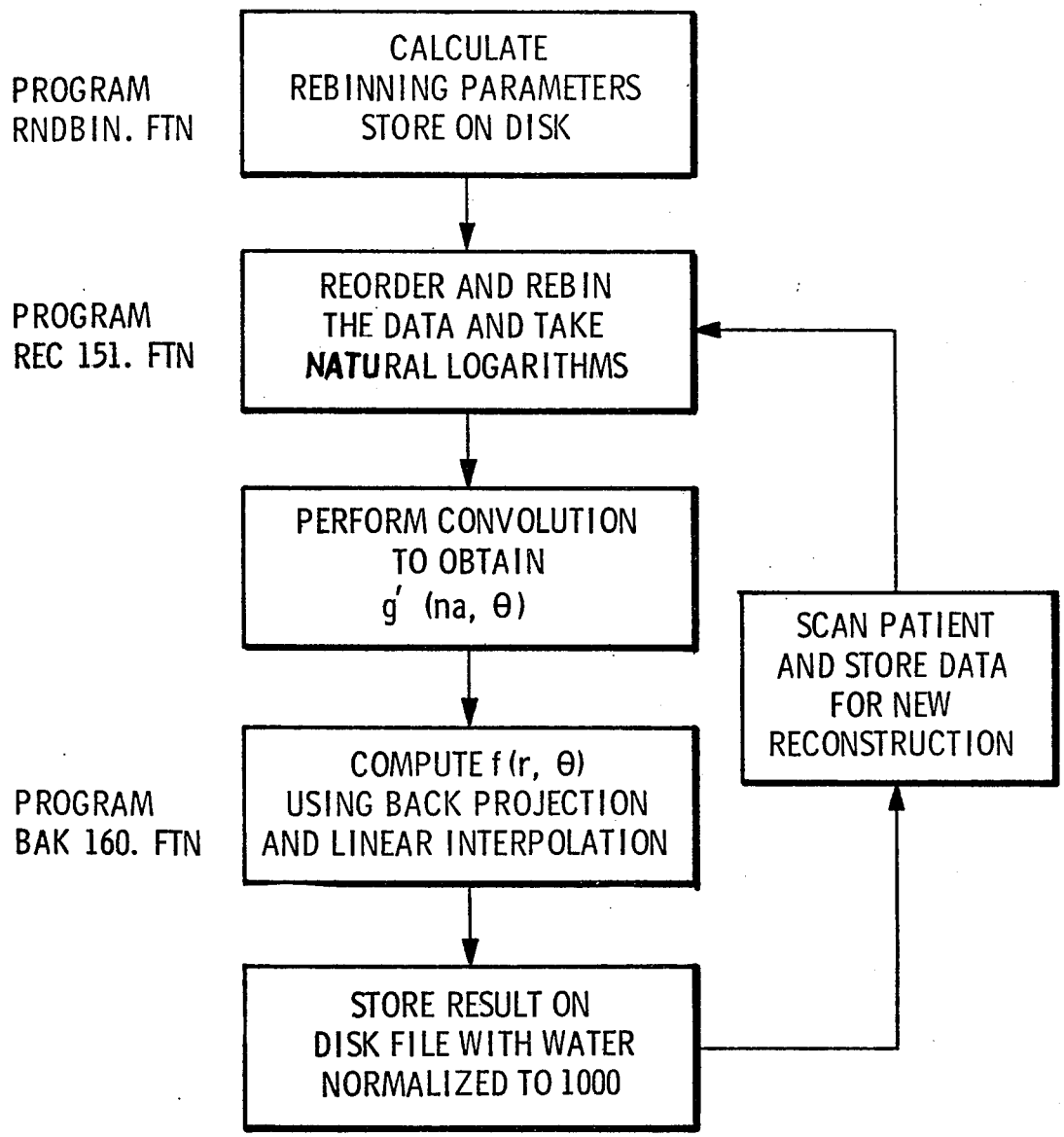
FIG. 22 is a flow chart for a computerized method for reconstruction of the 3-D tomographs.

The coordinates of the boundaries of the old bins illustrated in FIG. 13 may be calculated by an alternative method used by the computer program referred to in the flow chart of FIG. 22. The $x$ and $y$ axis are taken as a line passing through the center of rotation 33 in FIG. 6, and perpendicular to a particular series of parallel rays. The new bins are equally spaced as before. The old bins ($x$ axis) are defined by the intersection of the bounds of the actual fan rays with this line. For $n=2$, these bounds are typically given by lines at $+\frac{1}{4}°$ and $-\frac{1}{4}°$ with respect to a perpendicular line from each particular central source position 13 included in a parallel series. Typically the bins defined in this way are not immediately adjacent as in FIG. 13 but are separated by gaps. The bins representing slant rays are introduced by using rays bounded by lines at $-\frac{3}{4}°$ and $-\frac{1}{4}°$ with respect to a perpendicular line from each source position, and will be seen to fit into the spaces between the perpendicular rays, although insignificantly small gaps will remain. Bin boundaries defined in this way closely conform to those of the previous method, with small differences which improve the accuracy of the slant approximation. The $f_{ij}$ coefficients are now calculated by determining the amount of overlap of old bins with new bins as before.

disclosed in an article titled "Three Dimensional Reconstruction from Radiographs and Electron Micrographs: Application of Convolutions Instead of Fourier Transforms" appearing in the *Proceedings of the National Academy of Sciences, U.S.A.*, Vol. 68, No. 9, pages 2236-2240 of Sept. 1971. Briefly this method consists of transforming the parallel ray shadowgram data into shadowgram data corresponding to the natural logarithm $\ln$ of the intensity of the unmodified detected radiation as a function of $y$, namely $I'(y)$, normalized to The preferred computerized method for reconstructing the 3-D tomographs from the angularly displaced reordered sets of parallel ray shadowgraphs is a method the beam intensity $I_0(y)$. $I_0(y)$ is measured before the shadowgrams are made, by detecting the unabsorbed beam on each of the detector wires 53, and applying the reordering and rebinning transformations, and that information is stored in the computer for use in these calculations.

FIG. 14 shows a typical shadowgraph for the function $\ln I'(y)/I_0(y)$ which may be referred to as $g(na,\theta)$. The linear shadowgraphs for different angles $\theta$ are each scanned at intervals $a$ and these data are then convoluted with a function $q(na)$ to obtain $g'(na;\theta)$ using the following algorithm:

$$g'(na;\theta) = \left(\frac{1}{4a}\right)g(na;\theta) - \left(\frac{1}{\pi^2 a}\right) \sum_{p \text{ odd}} \frac{g[(n-p)a;\theta]}{p^2} \qquad \text{(Eq. 5)}$$

where $$q(na) = \frac{1}{4a} \text{ for } n = 0 \qquad \text{(Eq. 6)}$$

$$= \frac{1}{\pi^2 n^2 a} \text{ for } n \text{ odd}$$

$$= 0 \text{ for } n \text{ even}.$$

The function $q(na)$ is shown in FIG. 15 and the product of the function of FIG. 15 with the point 78 of the shadowgraph function of FIG. 14 is shown in FIG. 16. As can be seen from the shape of the function of FIG. 15, this function has zero value for even numbered intervals and drops off relatively quickly with interval number $n$ so that the convolution of the function of FIG. 15 with that of FIG. 14 need only be evaluated at a reasonably small number $n$ of intervals $a$ away from the point on function 14 being evaluated. The individual products of the function of FIG. 15 with $g(na,\theta)$ for each value of $y$ or $na$ of FIG. 14 are summed to derive the function $g'(na;\theta)$ of FIG. 17 this process is known mathematically as the convolution of $g(na,\theta)$ with $q(na)$ as expressed in Eq. (5). In other words, the result of Eq. (5) is shown in FIG. 17 for a given value of $\theta$. Thus, there is generated by the algorithm of Eq. (5) 180 sets of the functions of FIG. 17, one for each angularly spaced set of parallel ray shadowgraph data. These 180 shadowgraphs are then back projected for calculating the resultant 3-D reconstructed tomograph employing the following algorithm:

$$f(r,\phi) = \sum_{t=1}^{N} g'[r \cos(\phi - t\Delta\theta), t\Delta\theta] \quad \text{Eq. (7)}$$

where $t, N$ are integers. $r$ and $\phi$ are the polar coordinates of the individual reconstruction matrix elements. The interval for $\theta$ is $\Delta\theta = (180/N)°$, where N is the number of shadowgraphs recorded at regular intervals over the range of $-\pi/2$ to $+\pi/2$, typically 180. In Eq. (7), the value of $r \cos(\phi - t\Delta\theta)$ will not in general be a multiple of $a$; therefore a linear interpolation between the calculated values of $g'(na;\theta)$ is made so that the resolution of the final 3-D reconstructed data obtained for $f(r,\phi)$ will depend upon the fineness of the interval $a$ at which the shadowgraph data are available and the consequent accuracy of the interpolation.

This method of back projection is schematically indicated in FIG. 18. More particularly, the slice of the body 11 to be examined and for which a 3-D tomograph is to be reconstructed is considered to comprise a two dimensional matrix of elements 80 of equal size. In a typical example, the dimensions of the matrix elements are chosen equal to the spacing between adjacent anode wires 53, i.e., 2.5 mm. The reconstruction algorithm Eq. (7) consists of projecting the individual values of $g'(na,\theta)$ back across the matrix along lines perpendicular to the $y$ axis of the particular shadowgram.

This back projection process is conveniently accomplished as follows: The coordinates $r$, and $\phi$ for the center of a particular matrix element is calculated. The value of $y$ corresponding to the point on the axis of a particular projection intersected by a perpendicular line from the point $r,\phi$ is calculated. This is given by $r \cos (\phi - t\Delta\theta)$. The value of $g'(na,\theta)$ at that value of $y$ is calculated by means of linear interpolation between the two values of $g'(na,\theta)$ for which $na$ is nearest $y$. Hence $$g(y,\theta) = \left(\frac{a - y + ka}{a}\right) g'(ka,\theta) + \left(\frac{y - ka}{a}\right) g'[(k + 1) a,\theta]$$

where $k$ is the nearest integer less than $y/a$. This process is repeated N times for each value of $\theta$ and the sum of each projected value of $g(y,\theta)$ yields the value of $f(r,\phi)$ at that grid point. The value of $f(r,\phi)$ at other grid points is computed sequentially in a similar manner.

Referring now to FIG. 19 there is schematically indicated the problem of position uncertainty encountered when detecting a fan-shaped beam with a rectilinear array of position sensitive detecting elements 89. More particularly, as shown in FIG. 19 it is assumed that the detector 21 has some depth $d$ in the direction of the incoming rays 88. These rays are divergent and in addition intercept the rectilinear array at an acute angle. Assuming that the ray is divided into a multiplicity of detecting bins 89 it is seen that near the outer ends of the detecting array 21 a given ray may pass through more than one bin 89. Therefore, some uncertainty is introduced relative to the position of the detected ray.

In addition, the spacing $s$ taken along the length of the detector 21 between rays of equal anglular spacing $\psi$ increases toward the outer ends of the detector 21. Thus, each bin 89 near the ends tends to detect less radiation than bins near the center ray $r_{0,0}$ of the fan-shaped beam. Therefore, it is desirable to provide an improved position sensitive detector which will eliminate or substantially reduce the positional uncertainty factor and unequal spacing between rays as intercepted by a rectilinear detecting array of equal spacing between detector bin 89.

Referring now to FIGS. 20 and 21, there is shown an improved position sensitive detector 91 to replace the position sensitive detector 21 in the embodiment of FIGS. 1 and 6. In detector 91, the detector includes a gas-tight housing 92 formed by an arcuate channel structure including a pair of parallel arcuate sidewalls 93 and 94, as of stainless steel, closed on the bottom by a relatively narrow arcuate end wall 95. The open end of the channel structure is closed by means of a high strength thin metallic foil 96, as of nickel or stainless steel, which is brazed at 97 along one marginal side edge to an inside shoulder of sidewall 93 and to an arcuate rib portion 98 of side wall 94.

Opposite ends of the channel structure 92 are closed via end walls 103 and 104. A removable side wall portion 90 is secured via cap screws 102 to the bottom and end closing walls 95, 103 and 194 and to the arcuate rib 98 which bridges across between the end walls 103 and 104. An indium wire seal 101 extends around the periphery of the removable cover plate portion 90 for sealing same in a gas tight manner.

The conductive housing 92 forms the cathode electrode of the detector 91 and the anode electrode comprises an array of radially directed anode wires 53 centrally disposed of the chamber 92. Each anode wire 53 is supported between a pair of glass insulating terminals 105 and 106. Insulators 105 are supported from the removable cover plate 90 and the insulators 106 are feedthrough insulators for feeding the anode potential to the individual anode posts 107 through the envelope for connection to the respective amplifiers 65.

The chamber 92 is filled with an ionizable gaseous medium such as xenon to a pressure above atmospheric pressure, such as 5 atmospheres. The individual anode wires 53, as of stainless steel, have a diameter of 12.5 microns and a length of, for example, 10 centimeters. The anode wires 53 are spaced apart at $\frac{1}{2}°$ intervals of $\psi$ with a total of 151 wires 53. The projected center of the radial array of wires 53 is the source 13 so that the individual anode wires are arrayed parallel to the rays of penetrating radiation to be detected. This substantially reduces the uncertainty and unequal spacing problems as previously alluded to with regard to rectilinear detector arrays.

For a position sensitive detector 91 based upon the concept of capturing between 50 and 100% of the penetrating radiation of up to 100keV incident thereon, the product of the gas filled pressure, in atmospheres, times the length of the individual anode wires 53 should equal 50 atmosphere-centimeters. This means that the detector wires may be 1 centimeter long if the pressure fill is at 50 atmospheres. Alternatively, the gas fill may be 5 atmospheres if the length of the individual anode wires is 10 centimeters. Thus, the detector 91, as contrasted with the linear detector 21, provides increased spatial resolution and improved high efficiency operation for X-ray or γ-ray energies of 100keV and higher. Improving the spatial resolution, simplified the reconstruction of the X-ray shadowgraphic data into a 3-D tomograph.

The flow diagram for the computer program for carrying out the 3-D reconstruction according to the process described above with regard to FIGS. 10–18 is shown in FIG. 22 and actual computer reconstruction programs in Fortran language, are as follows:

```
C                             RNDBIN.FTN
COMMENT  RNDBIN IS THE FIRST OVERLAY OF A THREE PART PROGRAM TO
C    CALCULATE A 160 BY 160 RECONSTRUCTION, USING THE       FAN
C    BEAM CONVOLUTION TECHNIQUE, FROM 256 151-CHANNEL CURVED
C    SHADOWGRAPHS.  RNDBIN COMPUTES  THE MAPPING FROM A 151 CHANNEL 75.5
C    DEGREE CURVED DETECTOR TO A 151 BIN PARALLEL RAY SHADOWGRAPH.
C        ITS OUTPUT IS THE MAPPING STORED IN CHANEL(3,151) AND CHANFR
C    (3,151), WHICH ARE WRITTEN ON THE DISK (UNIT 3) IN THE FILE
C    'MAPPIN.151'.  THIS FILE IS THEN USED BY THE SECOND OVERLAY,
C    REC151.  RNDBIN NEED ONLY BE RUN ONCE FOR A GIVEN VALUE OF D1,
C    THE DISTANCE FROM THE SOURCE TO THE ROTATION CENTER, SINCE THE
C    MAPPING IS SAVED IN A DISK FILE.
C
C        VARIABLE DEFINITIONS.
C            DETLFT = LEFT SIDE OF RAY INTERSECTION  WITH LR
C            DETRIT = RIGHT SIDE OF RAY INTERSECTION WITH LR
C            BINLFT = LEFT SIDE OF A BIN
C            BINRIT = RIGHT SIDE OF A BIN
C            CHANEL(3,151) - THE CHANNEL --> BIN MAPPING
C            CHANFR(3,151) - THE CHANNEL --> BIN OVERLAP FOR THE
C                            CHANEL(I,BIN)-TH CHANNEL AND THE BIN-TH
C                            BIN.
C
       IMPLICIT DOUBLE (A-H),(O-Z)
       INTEGER BIN,RAY,LEFT,RIGHT,SIDE,CHANEL(3,151)
       REAL*4 CHANFR(3,151)
       COMMON /A2/CHANEL
       CALL SETFIL (3,'MAPPIN.151',IER,'SY',0)
       DEFINE FILE 3(6,302,U,IFILE3)

C
COMMENT    FROM HERE UNTIL 'DO 100' WE HAVE INITIALIZATIONS.
       DO 1 I=1,3
         DO 1 J=1,151
1          CHANEL(I,J) = 0
C
COMMENT   TWO RAYS EMANATE FROM EACH SOURCE POINT.  THE LEFT RAY
C    IS A WEDGE FROM -.75 DEGREES TO -.25 DEGREES AND THE RIGHT RAY
C    IS A WEDGE FROM -.25 DEGREES TO .25 DEGREES.  THEY ARE
C    REFERRED TO AS LEFT AND RIGHT RAYS.  THE VARIABLE SIDE REMEM-
C    BERS WHCIH TYPE WE WILL WORK WITH NEXT.
C
       LEFT = 1
       RIGHT = 2
       PI = 3.14159265D0
       DEGRAD = PI/180.D0
       DLTHET = 1.D0*DEGRAD
       D1 = 30.48D0
C
COMMENT  TAN25 AND TAN75 ARE USED TO COMPUTE THE INTERSECTIONS OF
C    THE RAYS WITH THE CENTER LINE LR.
C
       TAN25 = DSIN(.25D0*DEGRAD)/DCOS(.25D0*DEGRAD)
       TAN75 = DSIN(.75D0*DEGRAD)/DCOS(.75D0*DEGRAD)
       SINT = DSIN(-37.D0*DEGRAD)
       COST = DCOS(-37.D0*DEGRAD)

OFFSET = D1*(SINT-COST*TAN75)
       SINT = DSIN(30.D0*DEGRAD)
       COST = DCOS(30.D0*DEGRAD)
C
COMMENT   NOTE THAT DINMID IS LESS THAN THE WIDTH OF A RAY INTER-
C    SECTION WITH THE CENTER LINE FOR CENTER SOURCES AND GREATER
C    FOR EDGE SOURCES, SO THAT A BIN MAY BE ENTIRELY COVERED BY
C    A RAY, A BIN MAY COVER PARTS OF TWO RAYS, AND ON THE SIDES A
```

```
C       BIN MAY COVER A RAY AND OVERLAP THE RAYS TO EACH SIDE, CORRESPOND-
C       ING TO THE THREE CASES BELOW.
C
        BINWID = (D1*(SINT-COST*TAN25)-OFFSET)/151.D0
C       RAYANG IS THE ANGLE OF A SOURCE FROM THE PERPENDICULAR TO THE
C       SHADOWGRAPH.
        RAYANG = -38.D0*DEGRAD
        SIDE = LEFT
        DO 100 RAY = 1,151
          IF(SIDE.EQ.RIGHT) GOTO 110
C         IF SIDE .EQ. LEFT WE ARE AT A NEW SOURCE, AND NEED TO
C         INCREMENT THE SOURCE ANGLE, RAYANG.
          RAYANG = RAYANG+DLTHET
          SINT = DSIN(RAYANG)
          COST = DCOS(RAYANG)
          DETLFT = D1*(SINT-COST*TAN75)-OFFSET
          DETRIT = D1*(SINT-COST*TAN25)-OFFSET
          DETWID = DETRIT-DETLFT
          SIDE = RIGHT
          GOTO 120
COMMENT   ELSE
110       DETLFT = DETRIT
          DETRIT = D1*(SINT+COST*TAN25)-OFFSET
          DETWID = DETRIT-DETLFT
          SIDE = LEFT
120     BIN = DETLFT/BINWID+1
        IF ( BIN.LT.1) BIN = 1
        IF(BIN.GT.151) GOTO 100
        BINLFT = (BIN-1)*BINWID
        BINRIT = BINLFT+BINWID
        IF (DETLFT.LT.BINLFT) DETLFT=BINLFT
        IF(BINRIT.GT.DETRIT) GOTO 200
COMMENT   CASES A AND B.
          CALL CHANL(BIN,M,RAY)
          CHANFR(M,BIN) = (BINRIT-DETLFT)/DETWID
          BIN = BIN+1
          IF(BIN.GT.151) GOTO 100
          BINLFT = BINRIT
          BINRIT = BINRIT+BINWID
          CALL CHANL(BIN,M,RAY)
          IF ( DETRIT.LT.BINRIT) GOTO 170
COMMENT     CASE B - MIDDLE BIN.
            CHANFR(M,BIN) = BINWID/DETWID
            BIN = BIN+1
            IF(BIN.GT.151) GOTO 100
            BINLFT = BINRIT
            BINRIT = BINRIT+BINWID
            CALL CHANL(BIN,M,RAY)
COMMENT     CASES A AND B - RIGHT HAND BIN
170         CHANFR(M,BIN) = (DETRIT-BINLFT)/DETWID
            GOTO 220
COMMENT   ELSE CASE C.
200         CALL CHANL(BIN,M,RAY)
            CHANFR(M,BIN)=1.D0
220       CONTINUE
100     CONTINUE
        CHANFR(3,1) = BINWID
        DO 300 I = 1,3
          IFILE3 = I
          WRITE(3'IFILE3) (CHANEL(I,J), J=1,151)
          IFILE3 = I+3
          WRITE(3'IFILE3) (CHANFR(I,J), J=1,151)
300     CONTINUE
        CALL RUN ('DK0:REC151.LDA[3,5]')
        STOP
        END
```

ROUTINES CALLED:
SETFIL, DSIN , DCOS , CHANL , RUN

OPTIONS =/ON, /CK, /OP:3

BLOCK     LENGTH
MAIN.     1782    (006754)*
A2        453     (001612)

COMPILER ----- CORE
   PHASE        USED   FREE
DECLARATIVES   00622  10626
EXECUTABLES    01192  10056
ASSEMBLY       01480  14408

```
        SUBROUTINE CHANL(BIN, M, RAY)
COMMENT CHANL FINDS UNUSED POSITIONS IN CHANEL(M, BIN) FOR FIXED BIN
        INTEGER BIN, M, RAY, CHANEL(3, 151)
        COMMON /A2/CHANEL
        M = 1
10      IF (CHANEL(M, BIN).EQ.0) GOTO 20
        M = M+1
        GOTO 10
20      CHANEL(M, BIN)= RAY
        RETURN
        END
```

OPTIONS =/ON, /CK, /OP:3

BLOCK     LENGTH
CHANL     67      (000206)*
A2        453     (001612)

COMPILER ----- CORE
   PHASE        USED   FREE
DECLARATIVES   00622  10626
EXECUTABLES    00711  10537
ASSEMBLY       00924  14964

```
C                          REC151.FTN
COMMENT REC151 IS THE SECOND OVERLAY OF A THREE PART PROGRAM TO CAL-
C       CULATE A 150 BY 150 RECONSTRUCTION, USING THE     FAN BEAM CON-
C       VOLUTION TECHNIQUE, FROM 256 151-CHANNEL CURVED SHADOWGRAPHS AT
C       1.0 DEGREE ANGULAR SEP   NG WITH CHANNELS FROM -37.5 DEGREES TO
C       37.5 DEGREES AT .5 DEGREE INTERVALS.  THE MAPPING FROM 256 CURVED
C       SHADOWGRAPHS WAS COMPUTED BY THE FIRST OVERLAY, RNDBIN.FTN,
C       STORED ON THE DISK (UNIT 3) IN 'MAPPIN.151[3,5]' AND IS READ INTO
C       THE ARRAYS CHANEL(3,151) AND CHANFR(3,151).  THE BIN WIDTH,
C       ALSO COMPUTED BY RNDBIN, IS STORED IN CHANFR(3,1), AN UNUSED
C       POSITION IN THE MAPPING.  REC151 DOES THE REBINNING AND CONVOLU-
C       TION WITH THE BACK PROJECTION LEFT FOR THE THIRD OVERLAY, BAK160.
C          THE INPUT IS 257 RECORDS, EACH 151 WORDS LONG, ON UNIT 1.
C       THE ACTUAL FILE NAME IS ASSIGNED PRIOR TO EXECUTION.  THE OUTPUT
C       IS GPRIME(151,180), ON THE DISK (UNIT 4) IN FILE 'GPRIME.2'.
C
C       FILE DEFINITIONS:
C              FILE 1 - INPUT FILE, ASSIGNED PRIOR TO EXECUTION
C              FILE 3 - MAPPING FROM RNDBIN 'MAPPIN.151'
C              FILE 4 - OUTPUT FILE 'GPRIME.2'
C
C       VARIABLE DEFINITIONS:
C
C         CHANEL(3,151) - STORES CHANNEL --> BIN NUMBER
C         CHANFR(3,151) - STORES CHANNEL --> BIN OVERLAP
C         PHNOUT(151)   - PHANTOM OUT COUNTS IN RECORD 157 UNIT 1
C         KOUNTS(151,80)- STORES 80 CURVED SHADOWGRAPHS WITH THE PHANTOM
C                         IN.  READ FROM UNIT 1.
```

```
C      IO(151)      -   LOGARITHMS OF REBINNED PHANTOM OUT COUNTS
C      G(151)       -   REBINNED PARALLEL RAY SHADOWGRAPH MEASUREMENTS
C      GPRIME(151)  -   CONVOLVED SHADOWGRAPH.  STORED IN 'GPRIME.2'
C
       REAL CHANFR(3,151),IO(151),G(151),GPRIME(151),INVBIN
       INTEGER CHANEL(3,151),ANGLE,BIN,KOUNTS(151,80),PHNOUT(151)
      1    ,V1,ANGL,V4
       EQUIVALENCE (KOUNTS(1,1),PHNOUT(1))
       DEFINE FILE 1(257,151,U,V1)
       CALL SETFIL (3,'MAPPIN.151',IER,'SY',0)
       DEFINE FILE 3(6,302,U,IFILE1)
       CALL SETFIL(4,'GPRIME.2',IER,'SY',0)
       DEFINE FILE 4(180,302,U,ANGL)
C      READ IN THE MAPPING ROM THE DISK IN THE 500 LOOP.
       DO 500 I = 1,3
          IFILE1 = I
          READ(3'IFILE1) (CHANEL(I,J), J = 1,151)
          IFILE1 = I+3
          READ(3'IFILE1) (CHANFR(I,J), J=1,151)
500    CONTINUE
C      INITIALIZATIONS:
       BINWID = CHANFR(3,1)
       PI = 3.14159
       PIPI = 1./PI/PI
       DEGRAD = PI/180.
       RADDEG = 180./PI
       D1 = 12.*2.54
       INVBIN = 1./BINWID
COMMENT READ THE PHANTOM OUT COUNTS AND TAKE THEIR LOGA-
C      RITHMS IN THE 300 LOOP
       READ(1'257) PHNOUT
       DO 300 BIN = 1,151
          A = 0.
          DO 320 I=1,3
             IF(CHANEL(I,BIN).EQ.0) GOTO 320
             K = CHANEL(I,BIN)
             A = A+PHNOUT(K)*CHANFR(I,BIN)
320       CONTINUE
300       IO(BIN) = ALOG(A)
COMMENT DO THE REMAPPING OF THE THE PHANTOM IN MEASUREMENTS, ONE
C      PARALLEL RAY SHADOWGRAPH AT A TIME, IMMEDIATELY FOLLOWED BY CON-
C      VOLUTION.
C
COMMENT THERE IS NOT ENOUGH CORE TO HOLD ALL OF THE FAN SHADOW-
C      GRAPHS IN MEMORY AT ONCE, SO 80 OF THEM ARE USED AT A TIME
C      TO MAKE FIVE PARALLEL RAY SHADOWGRAPHS.  THIS MEANS THAT THE
C      THE REBINNING IS DONE IN THIRTY-SIX STEPS.
C
       V1 = 1
       I1 = 1
       I2 = 5
330    DO 340 J= 1,80
          READ(1'V1) (KOUNTS(I,J), I=1,151)
340    CONTINUE
       DO 350 ANGLE = I1,I2
          DO 360 BIN = 1,151
             A = 0.
             DO 370 I=1,3
                IF(CHANEL(I,BIN).EQ.0) GOTO 370
                K = CHANEL(I,BIN)
                L = ANGLE+(K+1)/2-I1
                A = A+KOUNTS(K,L)*CHANFR(I,BIN)
370          CONTINUE
             IF (A.LT.1) A=1.
             A = IO(BIN) -ALOG(A)
             IF (A.GT.20) A=20.
360          G(BIN) = A
```

```
COMMENT    G IS COMPLETELY FORMED FOR THIS ANGLE SO CONVOLUTE
C          IT INTO GP AND WRITE IT ON THE DISK.
           DO 380 BIN = 1,151
              U = 0.
              K = MAX0(BIN,151-BIN)
              DO 390 KK = 1,K,2
                 IF (BIN-KK. GE. 1) U = U+G(BIN-KK)/(KK*KK)
                 IF (BIN+KK. LE. 151) U = U+G(BIN+KK)/(KK*KK)
390           CONTINUE
380        GPRIME(BIN) = (G(BIN)*.25-U*PIPI)*INVBIN
           WRITE(4'ANGLE) GPRIME
350     CONTINUE
C
COMMENT   NOW GO BACK AND REBIN THE NEXT FIVE SHADOWGRAPHS.
          IF(I2. EQ. 180) GOTO 400
          I1 = I1+5
          I2 = I2+5
          V1 = I1
          GOTO 220
COMMENT PROCEED TO THE BACK PROJECTION BY THE NEXT OVERLAY, BAK160.
400       CALL RUN('DK0:BAK160. LDA(3,5)')
700       STOP
          END
ROUTINES CALLED:
SETFIL, ALOG , MAX0 , RUN

OPTIONS =/ON,/CK,/OP:3

BLOCK      LENGTH
MAIN.      15116   (073030)*

COMPILER ----- CORE
   PHASE       USED   FREE
DECLARATIVES  00622  10626
EXECUTABLES   01194  10054
ASSEMBLY      01547  14341

C                       BAK160. FTN(3,5)
COMMENT    BAK160. FTN IS THE THIRD OVERLAY, WHICH DOES THE BACK
C          PROJECTION, OF THE 160 BY 160 RECONSTRUCTION PROGRAM FOR THE
C          HEPL FAN BEAM CONVOLUTION TECHNIQUE.  IT IS CALLED BY REC151
C          AFTER THE CONVOLUTION IS COMPLETED.
C
C    ITS INPUT IS GPRIME, ON THE DISK (UNIT 1) WHICH WAS STORED
C    THERE BY REC151.  BECAUSE OF MAIN MEMORY LIMITATIONS IT IS READ
C    IN AND BACK PROJECTED IN FOUR SECTIONS.  'FTEMP. 160' ON UNIT 3
C    IS USED TO STORE THE PARTIAL RESULTS.  THE FINAL OUTPUT IS A
C    160 BY 160 INTEGER ARRAY ON UNIT 2.  THE ACTUAL FILE NAME IS
C    ASSIGNED PRIOR TO EXECUTION.
C    FILE DEFINITIONS:
C         FILE 2 - OUTPUT FILE, 160 BY 160 RECONSTRUCTION
C                    ASSIGNED PRIOR TO EXECUTION
C         FILE 3 - INPUT FILE 'GPRIME. 2'
C         FILE 4 - SCRATCH WORK FILE 'FTEMP. 160'
C
C
C    VARIABLE DEFINITIONS:
C      GPRIME(151,45) - CONVOLUTED MEASUREMENTS READ FROM FILE 1.
C                       THE 180 STEP BACK PROJECTION IS DONE 45 STEPS
C                       AT A TIME DUE TO STORAGE LIMITATIONS
C      FTEMP(160) -  TEMPORARY STORAGE FOR ONE ROW OF PARTIAL BACK
C                     PROJECTIONS.  A BUFFER FOR FILE 3.
C      DENSTY(160) - ONE ROW OF COMPLETED BACK PROJECTIONS; A BUFFER
C                     FOR FILE 2.  WATER DENSITY NORMALIZED TO 1000.
```

```
C        COSTAB(361) - COSINE TABLE FROM 0 DEGREES TO 360 DEGREES.
C                     USED TO GENERATE COS(THETA BY INTERPOLATION DUR-
C                     DURING THE BACK PROJECTION. WHEN IMPLEMENTED IN
C                     FORTRAN THE INTERPOLATION IS 50% SLOWER THAN
C                     CALLING THE COS FUNCTION, BUT IT IS MUCH FASTER
C                     WHEN IMPLEMENTED IN ASSEMBLY LANGUAGE, WHILE STILL
C                     PROVIDING SUFFICIENT ACCURACY.
C
C
         REAL GPRIME(151,45),FTEMP(160),COSTAB(361)
         INTEGER ANGLE,BIN,V4,ANGL,V2,DENSTY(160)
         DEFINE FILE 2(160,160,U,V2)
         CALL SETFIL (3,'GPRIME.2',IER,'SY',0)
         DEFINE FILE 3(180,302,U,ANGL)
         CALL SETFIL (4,'FTEMP.160',IER,'SY',0)
         DEFINE FILE 4(160,320,U,V4)
         PI = 3.14159
         DEGRAD = PI/180.
         RADDEG = 180./PI
         DLTHET = 1.0 * DEGRAD
C        COSTAB IS GENERATED HERE.
         DO 10 I= 1,361
            T = (I-1)*DEGRAD
10          COSTAB(I) =COS(T)*151./160.
C
COMMENT THE BACK PROJECTIONS IS EVALUTED 45 STEPS AT A TIME.
C     COS(THETA AND GPRIME(RO*COS(THETA-PHI),PHI) ARE EVALUATED
C     BY LINEAR INTERPOLATION.
C     RMAX IS THE RADIUS OF THE RECONSTRUCTION CIRCLE.
C
         RMAX = 74.*160./151.
         I1 = 0
400      DO 500 ANGLE = 1,45
            ANGL = ANGLE+I1
            READ(3'ANGL) (GPRIME(I,ANGLE),I=1,151)
500      CONTINUE
         DO 600 NY = 1,160
            IF (I1.EQ.0) GOTO 610
            READ(4'NY) FTEMP
            GOTO 615
610         DO 611 I = 1,160
611            FTEMP(I) = 0
615         B = NY-80.5
            BB = B*B
            DO 605 NX =1,160
               A = NX-80.5
               THETA = ATAN2(B,A)*RADDEG-I1
               IF ( THETA.LT.0. ) THETA = THETA+360.
               RO = SQRT(A*A+BB)
C              CHECK TO SEE IF (NX,NY) IS IN THE RECONSTRUCTION CIRCLE.
C              IF IT IS NOT, BRANCH TO 620 AND SET ITS DENSITY
C              TO ZERO.
               IF (RO.GT.RMAX) GO TO 620
               C = 0.
C              THE 650 LOOP DOES THE ACTUAL BACK PROJECTION.
               DO 650 I=1,45
                  THETA = THETA-1.
                  IF (THETA.LT.0) THETA = THETA+360.
                  J = THETA+1
C                 COSINE INTERPOLATION.
                  R = RO*(COSTAB(J)+(COSTAB(J+1)-COSTAB(J))
                         *(THETA+1-J))+76.
                  K = R
C                 GPRIME INTERPOLATION AND BACK PROJECTION FROM SHADOW-
C                 GRAPH I.
                  C = C+GPRIME(K,I)*(1+K-R)+GPRIME(K+1,I)*(R-K)
```

```
650            CONTINUE
C              FTEMP IS THE NY-TH ROW OF THE PARTIAL RECONSTRUCTION.
C              IT IS SAVED IN THE SCRATCH FILE 'FTEMP.160'.
               FTEMP(NX) = C+FTEMP(NX)
               GOTO 605
620            FTEMP(NX) = 0.
605            CONTINUE
606            IF (I1.NE.135) WRITE(4'NY) FTEMP
               IF(I1.NE.135) GOTO 600
COMMENT        STORE THE FINAL RESULT WITH WATER DENSITY NORMAL-
C              IZED TO 1000.
               DO 640 I=1,160
640            DENSTY(I) = FTEMP(I)*DLTHET*5000.
               WRITE(2'NY) DENSTY
600            CONTINUE
               IF (I1.EQ.135) GOTO 700
               I1 = I1+45
               GOTO 450
2              FORMAT(12I6)
700            STOP
               END

ROUTINES CALLED:
SETFIL, COS    , ATAN2 , SQRT

OPTIONS =/ON,/CK,/OP:3

BLOCK          LENGTH
MAIN.          15486   (074374)*

COMPILER ----- CORE
    PHASE        USED    FREE
DECLARATIVES    00622   10626
EXECUTABLES     01183   10065
ASSEMBLY        01563   14325
```

The advantage of the fan beam penetrating ray 3-D tomograph apparatus of the present invention, as contrasted with prior systems utilizing both angular rotation and transverse rectilinear translation, as exemplified by the aforecited U.S. Pat. No. 3,778,614, is that the lateral translation is eliminated and the resultant apparatus is substantially less complex. As a result, the time required to obtain the amount of shadowgraphic data required for high resolution, i.e., 1% accuracy 3-D reconstruction, is reduced to times less than a breath-holding period so that portions of the body subject to movement with breathing and the like can be obtained without blurring due to body movement. For example, the present invention permits 3-D tomographs to be obtained of the lungs without blurring due to movement.

What is claimed is:

1. In a method of penetrating ray tomography the steps of:

directing a divergent beam of penetrating radiation through a body to be analyzed from a source on one side of the body to a detector on the other side of the body:

effecting relative angular displacement between the divergent beam of penetrating radiation and the body;

detecting the penetrating radiation that has passed through the body at a number of angularly spaced positions within the angle subtended by the divergent beam for each angular position of the divergent beam relative to the body to derive sets of detected radiation data representative of a plurality of angularly spaced shadowgrams of absorption or transmission of the penetrating radiation by the body, each of said shadowgrams representing the transmission of the penetrating radiation through the body along an array of divergent paths subtended by the divergent beam, and different ones of said sets of angularly spaced sets of shadowgram data corresponding to different sets of intersecting rays of penetrating radiation; and reconstructing the sets of shadowgraphic data into a 3-D tomograph of the body under analysis.

2. In a method of examining at least a part of the interior of a body using penetrating radiation the steps of:

transmitting a divergent beam of radiation from an external source of radiation through the body in a plurality of divergent paths to establish an initial set of divergent ray paths through a generally planar slice of the body;

transmitting divergent radiation from said external source through said body in further sets of divergent paths disposed in said planar slice at different angles from each other and from said initial angle, the sets of divergent rays being such that every element of a two-dimensional matrix of elements of the body in said planar slice is intersected by a group of said rays, the group of rays being different for the different elements of the matrix;

deriving from each ray emerging from the body a discrete output signal representing the sum of the transmission or absorption of the elements of the body intersected by the ray to derive sets of discrete output signals corresponding to the sets of rays indicative of the transmission or absorption of elements of said matrix; and reconstructing from said discrete output signals a 3-D representation of the transmission or absorption of the elements of the matrix of the slice of the body.

3. In an apparatus for obtaining a 3-D tomograph of a body to be examined:

means for directing a divergent beam of penetrating radiation through the body to be examined from a source on one side of the body to a detector on the other side of the body;

means for detecting the divergent penetrating radiation that is passed through the body at a number of angularly spaced positions within the angle subtented by the divergent beam as a function of the relative angular position of the divergent beam relative to the body to derive sets of detected radiation data representative of sets of angularly spaced divergent ray shadowgrams of absorption or transmission of the divergent penetrating radiation by the body with different ones of said angularly spaced sets of the divergent ray shadowgram data corresponding to different sets of intersecting rays of divergent penetrating radiation.

4. The apparatus of claim 3 wherein said radiation detecting means is disposed in the divergent beam path of the penetrating radiation for detecting the divergent radiation after passage through the body; said detecting means including means responsive to the received penetrating radiation for deriving electrical signals representative of the intensity of the radiation as a function of the angular position within the divergent beam of penetrating radiation.

5. The apparatus of claim 4 wherein said radiation detecting means includes an array of spaced anode and cathode electrode means said array of electrode means extending laterally of and within the divergent path of penetrating radiation, means for containing an ionizable gaseous atmosphere in the space between said anode and cathode electrode means, and means for applying an operating electrical potential between the said anode and cathode electrode means for generating an electrical output signal in response to an ionizing event occasioned by absorption of a quantum of penetrating radiation by the ionizable gas in the space between said anode and cathode electrode means.

6. The apparatus of claim 3 wherein said means for directing a divergent beam of penetrating radiation through the body to be examined includes, means for directing a divergent fan-shaped beam of penetrating radiation onto the body, said fan-shaped beam of penetrating radiation, as directed onto the body, being of generally continuous uniform intensity across the fan-shaped subtended angle for a given radius from the apex of the fan-shaped beam.

7. The apparatus of claim 6 including, means for radially collimating the penetrating radiation emerging from the body, said collimating means being disposed between the body and said radiation detecting means.

8. The apparatus of claim 5 including an array of counter means operatively associated with said array of electrode means for separately summing the ionizing events separately detected by respective ones of said electrode means of said array of electrode means.

9. In a method of penetrating ray tomography the steps of;

directing a divergent fan-shaped beam of penetrating radiation through a body to be analyzed from a source on one side of the body to a detector on the other side of the body, the divergent fan-shaped beam of penetrating radiation having a generally continuous uniform intensity across the fan-shaped subtended angle for a given radius from the apex of the fan-shaped beam;

effecting relative angular displacement between the divergent beam of penetrating radiation and the body;

collimating the penetrating radiation emerging from the body while maintaining the generally continuous body-attenuated intensity thereof;

detecting the penetrating radiation that has passed through the body at a number of angularly spaced positions within the angle subtended by the divergent fan-shaped beam for each angular position of the divergent fan-shaped beam relative to the body to derive sets of detected radiation data representative of a plurality of angularly spaced shadowgrams of absorption or transmission of the penetrating radiation by the body, each of said shadowgrams representing the transmission of the penetrating radiation through the body along an array of divergent paths subtended by the divergent fan-shaped beam, and different ones of said sets of angularly spaced sets of shadowgram data corresponding to different sets of intersecting rays of penetrating radiation; and resonstructing the sets of shadowgraphic data into a tomograph of the body under analysis.

10. The method of claim 9 wherein the step of effecting relative angular displacement between divergent beam of penetrating radiation and the body comprises effecting said relative angular displacement in a manner which is substantially free of relative lateral translation therebetween.

11. In a method of examining at least a part of the interior of a body using penetrating radiation the steps of:

transmitting a divergent fan-shaped beam of radiation from an external source of radiation through the body in a plurality of divergent paths to establish an initial set of divergent ray paths through a generally planar slice of the body, the divergent fan-shaped beam of radiation having a generally continuous uniform intensity across the fan-shaped subtended angle for a given radius from the apex of the fan-shaped beam;

transmitting divergent fan-shaped radiation from said external source through said body in further sets of divergent paths disposed in said planar slice at different angles from each other and from said initial angle, the sets of divergent rays being such that every element of the two-dimensional matrix of elements of the body in said planar slice is intersected by a group of said rays, the group of rays being different for the different elements of the matrix;

collimating the penetrating radiation emerging from the body while maintaining the generally continuous uniform intensity thereof;

deriving from each ray emerging from the body a discrete output signal representing the sum of the transmission or absorption of the elements of the body intersected by the ray to derive sets of discrete output signals corresponding to the sets of rays indicative of the transmission or absorption of elements of said matrix; and reconstructing from said discrete output signals a representation of the transmission or absorption of the elements of the matrix of the slice of the body.

12. In an apparatus for obtaining a 3-D tomograph of a body to be examined:

means for directing a divergent beam of penetrating radiation through the body to be examined, said means including means for directing a divergent fan-shaped beam of penetrating radiation onto the body, being of generally continuous uniform intensity across the fan-shaped subtended angle for a given radius from the apex of the fan-shaped beam;

means for detecting the divergent penetrating radiation that is passed through the body at a number of angularly spaced positions within the angle subtended by the divergent beam as a function of the relative angular position of the divergent beam relative to the body to derive sets of detected radiation data representative of sets of angularly spaced divergent ray shadowgrams of absorption or transmission of the divergent penetrating radiation by the body with different ones of said angularly spaced sets of the divergent rays shadowgram data corresponding to different sets of intersecting rays of divergent penetrating radiation; and means, disposed between the body and said radiation detecting means, for collimating the penetrating radiation emerging from the body while maintaining the generally continuous body-attenuated intensity thereof as incident upon the radiation detecting means.

13. The apparatus of claim 12 wherein said collimating means radially collimates the penetrating radiation emerging from the body.

14. The apparatus of claim 13 wherein said radial collimator means includes a focused grid collimator having a plurality of collimating vanes for blocking scattered radiation emerging from the body.

15. The apparatus of claim 14 wherein said vanes are directed parallel to the spaced divergent rays emanating from said radiation directing means.

16. The apparatus of claim 14 wherein said radial collimator means further includes a slot collimator means between the body and said focused grid collimator, said slot collimator means comprising a narrow elongated slot in a radiation-absorbing material.

17. The apparatus of claim 12 wherein said collimator means comprises a narrow elongated slot in a radiation-absorbing material.

18. The apparatus of claim 12 wherein said means for directing a divergent beam of penetrating radiation through the body includes means for effecting relative angular displacement between the divergent beam of penetrating radiation and the body in a manner which is substantially free of relative lateral translation therebetween.

19. In an apparatus for obtaining a 3-D tomograph of a body to be examined:

means for directing a divergent beam of penetrating radiation onto and through the body to be examined;

means for detecting the divergent penetrating radiation that is passed through the body at a number of angularly spaced positions within the angle subtended by the divergent beam as a function of the relative angular position of the divergent beam relative to the body to derive sets of detected radiation data representative of sets of angularly spaced divergent ray shadowgrams of absorption or transmission of the divergent penetrating radiation by the body with different ones of said angularly spaced sets of the divergent ray shadowgram data corresponding to different sets of intersecting rays of divergent penetrating radiation, said radiation detecting means being disposed in the divergent beam path of the penetrating radiation for detecting the divergent radiation after passage through the body, said detecting means including means responsive to the received penetrating radiation for deriving electrical signals representative of the intensity of the radiation as a function of the angular position within the divergent beam of penetrating radiation and including an array of spaced anode and cathode electrode means, said array of electrode means extending laterally of and within the divergent path of penetrating radiation, means for containing an ionizable gaseous atmosphere in the space between said anode and cathode electrode means, and means for applying an operating electrical potential between the said anode and cathode electrode means for generating an electrical output signal in response to an ionizing event occasioned by absorption of an quantum of penetrating radiation by the ionizable gas in the space between said anode and cathode electrode means.

20. The apparatus of claim 19 including an array of summing means operatively associated with said array of electrode means for separately summing the ionizing events separately detected by respective ones of said electrode means of said array of electrode means.

21. The apparatus of claim 19 wherein said means for directing a divergent beam of penetrating radiation through the body includes means for effecting relative angular displacement between the divergent beam of penetrating radiation and the body in a manner which is substantially free of relative lateral translation therebetween.

* * * * *

UNITED STATES PATENT AND TRADEMARK OFFICE
CERTIFICATE OF CORRECTION

PATENT NO. : 4,075,492

DATED : February 21, 1978

INVENTOR(S) : Douglas P. Boyd and Michael B. Goitein

It is certified that error appears in the above-identified patent and that said Letters Patent are hereby corrected as shown below:

Column 10, lines 1-20, should read:

--The preferred computerized method for reconstructing the 3-D tomographs from the angularly displaced reordered sets of parallel ray shadowgraphs is a method disclosed in an article titled "Three Dimensional Reconstruction from Radiographs and Electron Micrographs: Application of Convolutions Instead of Fourier Transforms" appearing in the Proceedings of the National Academy of Sciences, U. S. A., Vol. 68, No. 9, pages 2236-2240 of September 1971. Briefly this method consists of transforming the parallel ray shadowgram data into shadowgram data corresponding to the natural logarithm ln of the intensity of the unmodified detected radiation as a function of y, namely $I'(y)$, normalized to the beam intensity $I_0(y)$. $I_0(y)$ is measured before the shadowgrams are made, by

UNITED STATES PATENT AND TRADEMARK OFFICE
CERTIFICATE OF CORRECTION

PATENT NO. : 4,075,492
DATED : February 21, 1978
INVENTOR(S) : Douglas P. Boyd and Michael B. Goitein Page 2 of 2

It is certified that error appears in the above-identified patent and that said Letters Patent are hereby corrected as shown below:

detecting the unabsorbed beam on each of the detector wires 53, and applying the reordering and rebinning transformations, and that information is stored in the computer for use in these calculations.--

Signed and Sealed this

Nineteenth Day of August 1980

[SEAL]

Attest:

SIDNEY A. DIAMOND

Attesting Officer

Commissioner of Patents and Trademarks

Notice of Adverse Decision in Interference

In Interference No. 100,325, involving Patent No. 4,075,492, D. P. Boyd and M. Goitein, FAN BEAM X-OR GAMMA-RAY 3-D TOMOGRAPHY, final judgment adverse to the patentees was rendered Aug. 22, 1983, as to claims 1-4, 6, 7, 9-15 and 18.

[*Official Gazette February 7, 1984.*]